US007485461B2

(12) United States Patent
Hammer

(10) Patent No.: US 7,485,461 B2
(45) Date of Patent: Feb. 3, 2009

(54) **CIS-ACTING REGULATORY ELEMENTS FROM *TRIPSACUM DACTYLOIDES***

(75) Inventor: Philip E. Hammer, Cary, NC (US)

(73) Assignee: Athenix Corporation, Research Triangle Park, NC (US)

( * ) Notice: Subject to any disclaimer, the term of this patent is extended or adjusted under 35 U.S.C. 154(b) by 121 days.

(21) Appl. No.: 11/377,318

(22) Filed: Mar. 16, 2006

(65) Prior Publication Data

US 2006/0218662 A1 Sep. 28, 2006

Related U.S. Application Data

(60) Provisional application No. 60/662,293, filed on Mar. 16, 2005.

(51) Int. Cl.
*A01H 5/00* (2006.01)
*A01H 5/10* (2006.01)
*C12N 15/29* (2006.01)

(52) U.S. Cl. .................. 435/419; 435/320.1; 536/24.1; 800/279; 800/298; 800/300

(58) Field of Classification Search ........................ None
See application file for complete search history.

(56) References Cited

U.S. PATENT DOCUMENTS

| | | | |
|---|---|---|---|
| 5,510,474 A | 4/1996 | Quail et al. | |
| 5,614,399 A | 3/1997 | Quail et al. | |
| 5,641,876 A | 6/1997 | McElroy et al. | |
| 5,907,086 A * | 5/1999 | Neill et al. | 800/295 |
| 6,020,190 A | 2/2000 | Quail et al. | |
| 6,054,574 A | 4/2000 | Quail et al. | |
| 6,528,701 B1 | 3/2003 | Wang et al. | |

FOREIGN PATENT DOCUMENTS

| | | |
|---|---|---|
| EP | 0 342 926 A | 11/1989 |
| WO | WO 01/94394 A2 | 12/2001 |

OTHER PUBLICATIONS

Kim et al., (1994) A 20 nucleotide upstream element is essential for the nopaline synthase (nos) promoter activity. Plant Molecular Biology 24: 105-117.*
Hannenhalli et al., (2001) Promoter prediction in the human genome. Bioinformatics 17: S90-S96.*
Hauschild, et al (1998) Isolation and analysis of the gene bbe1 encoding the berberine bridge enzyme from the California poppy *Eschscholzia californica* Plant Molec. Biol. 36:473-478.*
Maiti et al., (1997) Promoter/leader deletion analysis and plant expression vectors with the figwort mosaic virus (FMV) full length transcript (FLt) promoter containing single or double enhancer domains Transgen. Res., 6:143-156.*

Doelling et al (1995) The minimal ribosomal RNA gene promoter of *Arabidopsis thaliana* includes a critical element at the transcription initiation site 8 (5) 683-692).*
Liu et al (1995) Identity_Nuc Database. Accession No. ZMu29159 Jul. 20, 1995.*
Christensen, A.H., et al., "Maize Polyubiquitin Genes: Structure, Thermal Perturbation of Expression and Transcript Splicing, and Promoter Activity Following Transfer to Protoplasts by Electroporation," *Plant Molecular Biology*, 1992, pp. 675-689, vol. 18.
Christensen, A. H. and P.H. Quail, "Ubiquitin Promoter-Based Vectors for High-Level Expression of Selectable and/or Screenable Marker Genes in Monocotyledonous Plants," *Transgenic Research*, 1996, pp. 213-218, vol. 5.
Garbarino, J.E., et al., "Isolation of a Polyubiquitin Promoter and Its Expression in Transgenic Potato Plants," *Plant Physiol.*, 1995, pp. 1371-1378, vol. 109.
Hoisington, D., et al., "Plant Genetic Resources: What Can They Contribute Toward Increased Crop Productivity?," *Proc. Natl. Acad. Sci, USA*, 1999, pp. 5937-5943, vol. 96.
Plesse, B., et al., "Identification of a New *cis*-Regulatory Element in a *Nicotiana tabacum* Polyubiquitin Gene Promoter," *Mol. Gen. Genet.*, 1997, pp. 258-266, vol. 254.
Wang, J., et al., "Structure, Expression and Promoter Activity of Two Polyubiquitin Genes from Rice (*Oryza sativa* L.)," *Plant Science*, 2000, pp. 201-211, vol. 156.
Wei, H., et al., "Differential Expression of Sugarcane Polyubiquitin Genes and Isolation of Promoters from Two Highly-Expressed Members of the Gene Family," *J. Plant Physiol.*, 1999, pp. 513-519, vol. 155.
GenBank Report for Accession No. U29159, Direct Submission on Jun. 14, 1995.
Golenberg, E.M., et al., "Evolution of a Noncoding Region of the Chloroplast Genome," *Molecular Phylogenetics and Evolution*, Mar. 1993, pp. 52-64, vol. 2, No. 1.
Salgueiro, S., et al., "Intron-mediated *gusA* Expression in Tritordeum and Wheat Resulting from Particle Bombardment," *Plant Molecular Biology*, Mar. 2000, pp. 615-622, vol. 42, No. 4.
Wang, J., and J. H. Oard, "Rice Ubiquitin Promoters: Deletion Analysis and Potential Usefulness in Plant Transformation Systems," *Plant Cell Rep*, Sep. 2003, pp. 129-134, vol. 22, No. 2.

* cited by examiner

*Primary Examiner*—David H Kruse
(74) *Attorney, Agent, or Firm*—Alston & Bird LLP

(57) ABSTRACT

The present invention provides compositions and methods for regulating expression of heterologous nucleotide sequences in a plant. Compositions include a novel promoter nucleotide sequence for the gene encoding ubiquitin in *Tripsacum dactyloides*, as well as vectors, microorganisms, plants and plant cells having the promoter nucleotide sequence, or variants and fragments thereof. Methods for expressing a heterologous nucleotide sequence in a plant using the promoter sequences disclosed herein are also provided. The methods include stably incorporating into the genome of a plant cell a nucleotide sequence operably linked to the promoter of the present invention and regenerating a stably transformed plant that expresses the nucleotide sequence.

26 Claims, 9 Drawing Sheets

```
   1  AGCCGCCCTC TTTACGTTTG GCACGGTTTA TCTGAATCCG GCATGGCAAG TTAGACCGCA
  61  GTGCAGTGTG AGCCGGCCAC CGCAAGCTAG ACTGCTGTGC TGTGCCCCTC TCTGAAGAGT
 121  GAAGACTAAA GGCCAGCCGA TGAGCCGAGC ATGGTGACAG CAGCATGACC CTATAGTTTT
 181  TATCTTTCTT AGTGTGTGTG TGTGTGTGTG TGTGTGTGTG TGACTATGTG AGTAATGATT
 241  TTAGATCTGT GAGAGGGACA AAAGAAATAA TATTGCTACA TACTTTGAAG GTTGCGGCAT
 301  CTTTCTCCAA AATGTTTTGG TTTGTTGTCT AAGGACTAAG GCATTTGAAA GTCTAATTGC
 361  TCAAGATTCG ACAATTGGGA CGTCCTAAAG ATTAGTAAAT TCTATAGGGT TGATAACGTC
 421  TTATTTGGCT GGTCCTTTTT TTTTTCATGT TCCAACTCTA GTTTTTTGGA TGAAACTTTA
 481  CCAAATACTA ACTTAAGAAG TAATTTAGGA GAGAAGCTTT AAAGAGTATA ATCCATTTTT
 541  ATGCTATAAG AGTGAAGTCG TCATCAATCT AGGGTCTGTT TAGGAGAGCT TCACTTCAAG
 601  AATTTTAGGC TCGTTCCAAC TTCTTCCATC TAAACAGGTC TAGCTCCACG AGCTCTAACC
 661  TTGAAAAAAA AATTGAAACT AGAAGTCAGC TTCATGAAAT TCACGAAGCT CCCCAAGGGG
 721  TGCTTCACAA ACACTAATTT CATACCTTCT CATGGAGTTG CACGAGAACT ACCCACCATG
 781  TCACCGATTA CACAACGTAC CGCTTCGGCT CTCTCGTGAC AGCTCACTGA TCATCAAGGG
 841  CAATCAAGGA AACTCACAAA AATCAATTTT ATTATAGAAG CTGGAGTCCG CGCCCAAGCC
 901  AAACACTCCT CGAACTCACC TTAACAATTT GTTGAAGCTA TTTTATGATG AAATTGGAAA
 961  ACCGAAGCTG AAATTTTTGA AGTAAAACCC TCACAAACAG CCTCGTAGAT CCTGACTGTT
1021  TTTTTTCCCA AAAAGTTTC  ACCTATATAA TACTCCATCC GCCCAAAAT  ATAGTTCTTT
1081  CTAGCCCTCT TTTTTTTCGT CCACATACAA ATGAATGATA ATAAATCTAG ACATACATAT
1141  CAACCACATT CTTAGATTTA CTAATGAATG TATGTTTAGT CTAAAAAGAA TACTATTTTG
1201  GGACTGAGGG AGTAACAAAT AAAAAAACTA AGAAACCAT  GTACAGTGAG TGGCTTTACC
1261  CAATTGCCCT CCCCTCTAAT CCTTTTTTCC AGTAGATAAT GACAGGCGGG GCTAGTTCAA
1321  CGGCGTCGAC GAGTCTAACG GACCACAACC AGCGAACCAC CAGCGCGCCG GGCCAAGCGA
1381  AGCAGACGGC ACGGGTATCT CCGTCGCTGC CTGTGGACCC CTCCCCAGAG TTCCGCTCCA
1441  CCGGTGGCGG TTTCCAAGTC CATTCCGCAT TTCCGCCGTC GCGTTGGACT TGTTCCCCGC
1501  TGTCGGCATC CAGAAATTGC GTGGCGGAGC GGCAGGCGGC AGGCGGCACG GCAGGCGGCC
1561  TCCTCCTCCT TCGCAGCACG GGGGGATTCC TTTCCCACCG CCCCTTCGCT TTCCCTTCCT
1621  CGCCCGCCGT CATAAATAGA CACCCCCTCC TCAGCCTCTT TCCCCAACCT CAGCTTCTCT
1681  CGTGTTGTTC GGAGCGCACA CACACACAAC CAGATCTCTT CCCCCAAATC TCCTCGTCGA
1741  TCCCCCCCGC TTCAAGgtac ggcgatcatc ctccctccct ctctctacct tctctagatc
1801  ggcgatccga tccatggtta gggcccggca attctgttcc tgtctgtgtt acatccgtgc
1861  tgctagtgtt cgtacatgga tgcgacctgt aaacggtaaa ccagacacgt tctggttgct
1921  aacttgtcag tactctttgg ggaatcctgg gatggctcta gccgttccgc agacgggata
1981  gatttcacga tttgctttt  ttttgttgtt gccgcctagg ttttgtttg  cgttttttt
2041  ttattccgta tatgccgtgc tggtagatcg tgctacttac gttatgtgca cttgtttgtc
2101  gggtcatttt gtcatgtttt tttgttgttg tgatgatgtg gtctgattgg gctgtcgttc
2161  tagatcggag tagaataatg tgtcaaacta cctcgtagat tttttaaaa  aaaaattcgg
2221  atttgtatgt gtgtgtcata catcttcata gttaagaact taagatgatg gatggaaata
2281  tcgatcttta gataaggata ggtatacatg tcgatgtggg tttaactggt acctcggtag
2341  atgtattgct ctaacatgct ttagatgatg gcatatgcag catctgttca tatgctctaa
2401  catgctctaa ccttgagtac ctatctatca taataaacaa gtatgtttta taattatttg
2461  atcttgatac acttggatga tggtatatgc agcagctatg tcttgatttt tgccctgcct
2521  tcatgtgctg tttatttgct tgggactgtt cttttgttga tgctcaccct gtttggtgtt
2581  ccttctgcaG ATG CAG ATC TTT GTG AAG ACC CTG ACT GGC AA
```

FIG. 1

```
   1 AAGCTTTAAA GAGTATAATC CATTTTTATG CTATAAGAGT GAAGTCGTCA TCAATCTAGG
  61 GTCTGTTTAG GAGAGCTTCA CTTCAAGAAT TTTAGGCTCG TTCCAACTTC TTCCATCTAA
 121 ACAGGTCTAG CTCCACGAGC TCTAACCTTG AAAAAAAAAT TGAAACTAGA AGTCAGCTTC
 181 ATGAAATTCA CGAAGCTCCC CAAGGGGTGC TTCACAAACA CTAATTTCAT ACCTTCTCAT
 241 GGAGTTGCAC GAGAACTACC CACCATGTCA CCGATTACAC AACGTACCGC TTCGGCTCTC
 301 TCGTGACAGC TCACTGATCA TCAAGGGCAA TCAAGGAAAC TCACAAAAAT CAATTTTATT
 361 ATAGAAGCTG GAGTCCGCGC CCAAGCCAAA CACTCCTCGA ACTCACCTTA ACAATTTGTT
 421 GAAGCTATTT TATGATGAAA TTGGAAAACC GAAGCTGAAA TTTTTGAAGT AAAACCCTCA
 481 CAAACAGCCT CGTAGATCCT GACTGTTTTT TTTCCCAAAA AAGTTTCACC TATATAATAC
 541 TCCATCCGCC CCAAAATATA GTTCTTTCTA GCCCTCTTTT TTTTCGTCCA CATACAAATG
 601 AATGATAATA AATCTAGACA TACATATCAA CCACATTCTT AGATTTACTA ATGAATGTAT
 661 GTTTAGTCTA AAAAGAATAC TATTTTGGGA CTGAGGGAGT AACAAATAAA AAAACTAAAG
 721 AAACCATGTA CAGTGAGTGG CTTTACCCAA TTGCCCTCCC CTCTAATCCT TTTTTCCAGT
 781 AGATAATGAC AGGCGGGGCT AGTTAACGG CGTCGACGAG TCTAACGGAC CACAACCAGC
 841 GAACCACCAG CGCGCCGGGC CAAGCGAAGC AGACGGCACG GGTATCTCCG TCGCTGCCTG
 901 TGGACCCCTC CCCAGAGTTC CGCTCCACCG GTGGCGGTTT CCAAGTCCAT TCCGCATTTC
 961 CGCCGTCGCG TTGGACTTGT TCCCGCTGT CGGCATCCAG AAATTGCGTG GCGGAGCGGC
1021 AGGCGGCAGG CGGCACGGCA GGCGGCCTCC TCCTCCTTCG CAGCACGGGG GGATTCCTTT
1081 CCCACCGCCC CTTCGCTTTC CCTTCCTCGC CCGCCGTCAT AAATAGACAC CCCCTCCTCA
1141 GCCTCTTTCC CCAACCTCAG CTTCTCTCGT GTTGTTCGGA GCGCACACAC ACACAACCAG
1201 ATCTCTTCCC CCAAATCTCC TCGTCGATCC CCCCCGCTTC AAGgtacggc gatcatcctc
1261 cctccctctc tctaccttct ctagatcggc gatccgatcc atggttaggg cccggcaatt
1321 ctgttcctgt ctgtgttaca tccgtgctgc tagtgttcgt acatggatgc gacctgtaaa
1381 cggtaaacca gacacgttct ggttgctaac ttgtcagtac tctttgggga atcctgggat
1441 ggctctagcc gttccgcaga cgggatagat ttcacgattt gcttttttt tgttgttgcc
1501 gcctaggttt tgtttgcgt ttttttta ttccgtatat gccgtgctgg tagatcgtgc
1561 tacttacgtt atgtgcactt gtttgtcggg tcatttgtc atgttttttt gttgttgtga
1621 tgatgtggtc tgattgggct gtcgttctag atcggagtag aataatgtgt caaactacct
1681 cgtagatttt tttaaaaaaa aattcggatt tgtatgtgtg tgtcatacat cttcatagtt
1741 aagaacttaa gatgatggat ggaaatatcg atctttagat aaggataggt atacatgtcg
1801 atgtgggttt aactggtacc tcggtagatg tattgctcta acatgcttta gatgatggca
1861 tatgcagcat ctgttcatat gctctaacat gctctaacct tgagtaccta tctatcataa
1921 taaacaagta tgttttataa ttatttgatc ttgatacact tggatgatgg tatatgcagc
1981 agctatgtct tgattttgc cctgccttca tgtgctgttt atttgcttgg gactgttctt
2041 tgttgatgc tcaccctgtt tggtgttcct tctgcaG
```

FIG. 2

```
   1 GCGCTTTAAA GAGTATAATC CATTTTTATG CTATAAGAGT GAAGTCGTCA TCAATCTAGG
  61 GTCTGTTTAG GAGAGCTTCA CTTCAAGAAT TTTAGGCTCG TTCCAACTTC TTCCATCTAA
 121 ACAGGTCTAG CTCCACGAGC TCTAACCTTG AAAAAAAAAT TGAAACTAGA AGTCAGCTTC
 181 ACGAAATTCA CGAAGCTCCC CAAGGGGTGC TCCACAAACA CTAATTTCAT ACCTTCTCAT
 241 GGAGTTGCAC GAGAACTACC CACCATGTCA CCGATTACAC AACGTACCGC TTCGGCTCTC
 301 TCGTGACAGC TCACTGATCA TCGAGGGCAA TCAAGGAAAC TCACAAAAAT CAATTTTATT
 361 ATAGAAGCTG GAGTCCGCGC CCAAGCCAAA CACTCCTCGA ACTCACCTTA ACAATTTGTT
 421 GAAGCTATTT TATGATGAAA TTGGAAAACC GAAGCTGAAA TTTTTGAAGT AAAACCCTCA
 481 CAAACAGCCT CGTAGATCCT GACTGTTTTT TTTCCCAAAA AAGTTTCACC TATATAATAC
 541 TCCATCCGCC CCAAAATATA GTTCTTTCTA GCCCTCTTTT TTTTCGTCCA CATACAAATG
 601 AATGATAATA AATCTAGACA TACATATCAA CCACATTCTT AGATTTACTA ATGAATGTAT
 661 GTTTAGTCTA AAAAGAATAC TATTTTGGGA CTGAGGGAGT AACAAATAAA AAAACTAAAG
 721 AAACCATGTA CAGTGAGTGG CTTTACCCAA TTGCCCTCCC CTCTAATCCT TTTTTCCAGT
 781 AGATAATGAC AGGCGGGGCT AGTTCAACGG CGTCGACGAG TCTAACGGAC CACAACCAGC
 841 GAACCACCAG CGCGCCGGGC CAAGCGAAGC AGACGGCACG GGTATCTCCG TCGCTGCCTG
 901 TGGACCCCTC CCCAGAGTTC CGCTCCACCG GTGGCGGTTT CCAAGTCCAT TCCGCATTTC
 961 CGCCGTCGCG TTGGACTTGT TCCCCGCTGT CGGCATCCAG AAATTGCGTG GCGGAGCGGC
1021 AGGCGGCAGG CGGCACGGCA GGCGGCCTCC TCCTCCTTCG CAGCACGGGG GGATTCCTTT
1081 CCCACCGCCC CTTCGCTTTC CCTTCCTCGC CCGCCGTCAT AAATAGACAC CCCCTCCTCA
1141 GCCTCTTTCC CCAACCTCAG CTTCTCTCGT GTTGTTCGGA GCGCACACAC ACACAACCAG
1201 ATCTCTTCCC CCAAATCTCC TCGTCGATCC CCCCGCTTC AAGgtacggc gatcatcctc
1261 cctccctctc tctaccttct ctagatcggc gatccgatcc atggttaggg cccggcaatt
1321 ctgttcctgt ctgtgttaca tccgtgctgc tagtgttcgt acatggatgc gacctgtaaa
1381 cggtaaacca gacacgttct ggttgctaac ttgtcagtac tctttgggga atcctggat
1441 ggctctagcc gttccgcaga cgggatagat ttcacgattt gcttttttt tgttgttgcc
1501 gcctaggttt ttgtttgcgt tttttttta ttccgtatat gccgtgctgg tagatcgtgc
1561 tacttacgtt atgtgcactt gtttgtcggg tcatttgtc atgttttttt gttgttgtga
1621 tgatgtggtc tgattgggct gtcgttctag atcggagtag aataatgtgt caaactacct
1681 cgtagatttt tttaaaaaaa aattcggatt tgtatgtgtg tgtcatacat cttcatagtt
1741 aagaacttaa gatgatggat ggaaatatcg atctttagat aaggataggt atacatgtcg
1801 atgtgggttt aactggtacc tcggtagatg tattgctcta acatgcttta gatgatggca
1861 tatgcagcat ctgttcatat gctctaacat gctctaacct tgagtaccta tctatcataa
1921 taaacaagta tgttttataa ttatttgatc ttgatacact tggatgatgg tatatgcagc
1981 agctatgtct tgattttgc cctgccttca tgtgctgttt atttgcttgg gactgttctt
2041 ttgttgatgc tcaccctgtt tggtgttcct tcgtcaG
```

```
Trip5-Hind  : GTTGTTCGGAGCGGCCACACACACAACCAGATCTCTTCCCCAAATCTCCTCGTCGATCATCCCTCCTCGCTTCAAGGTACGGCGATCATCCCCCCGCTTCAAGGTACGGGGATCATCCCCTCCTCGCTTCTCTAGATC : 1287
Trip5B-Hin  : GTTGTTCGGAGCGGCCACACACACAACCAGATCTCTTCCCCAAATCTCCTCGTCGATCATCCCTCCTCGCTTCAAGGTACGGCGATCATCCCCCCGCTTCAAGGTACGGGGATCATCCCCTCCTCGCTTCTCTAGATC : 1287
Trip5C-Hin  : GTTGTTCGGAGCGGCCACACACACAACCAGATCTCTTCCCCAAATCTCCTCGTCGATCATCCCTCCTCGCTTCAAGGTACGGCGATCATCCCCCCGCTTCAAGGTACGGGGATCATCCCCTCCTCGCTTCTCTAGATC : 1287
Trp5_varie  : GTTGTTCGGAGCGGCCACACACACAACCAGATCTCTTCCCCAAATCTCCTCGTCGATCATCCCTCCTCGCTTCAAGGTACGGCGATCATCCCCCCGCTTCAAGGTACGGGGATCATCCCCTCCTCGCTTCTCTAGATC : 1287

Trip5-Hind  : GGCGATCCGATCCATGGTTAGGGCCCGGCCCGGCAATTCGTTCCTGTCGTGTTACATCCGTGCTGCTAGTCGTGCTGCTGTTCGTTACATGGATGCGACCTGTAAACGGTAAACCAGACACGTTCTGGTT : 1404
Trip5B-Hin  : GGCGATCCGATCCATGGTTAGGGCCCGGCCCGGCAATTCGTTCCTGTCGTGTTACATCCGTGCTGCTAGTCGTGCTGCTGTTCGTTACATGGATGCGACCTGTAAACGGTAAACCAGACACGTTCTGGTT : 1404
Trip5C-Hin  : GGCGATCCGATCCATGGTTAGGGCCCGGCCCGGCAATTCGTTCCTGTCGTGTTACATCCGTGCTGCTAGTCGTGCTGCTGTTCGTTACATGGATGCGACCTGTAAACGGTAAACCAGACACGTTCTGGTT : 1404
Trp5_varie  : GGCGATCCGATCCATGGTTAGGGCCCGGCCCGGCAATTCGTTCCTGTCGTGTTACATCCGTGCTGCTAGTCGTGCTGCTGTTCGTTACATGGATGCGACCTGTAAACGGTAAACCAGACACGTTCTGGTT : 1404

Trip5-Hind  : GCTAACTTGTCAGTACTCTTTGGGAATCCTGGGATGGCTCTAGCGCTTCCGCAGCCGTTCCGCAGACGGGATAGATTTCACGATTTGCTTTTTTTTTTGTTTGCCGCCTAGGTTTTTGTTTGCGTT : 1521
Trip5B-Hin  : GCTAACTTGTCAGTACTCTTTGGGAATCCTGGGATGGCTCTAGCGCTTCCGCAGCCGTTCCGCAGACGGGATAGATTTCACGATTTGCTTTTTTTTTTGTTTGCCGCCTAGGTTTTTGTTTGCGTT : 1521
Trip5C-Hin  : GCTAACTTGTCAGTACTCTTTGGGAATCCTGGGATGGCTCTAGCGCTTCCGCAGCCGTTCCGCAGACGGGATAGATTTCACGATTTGCTTTTTTTTTTGTTTGCCGCCTAGGTTTTTGTTTGCGTT : 1521
Trp5_varie  : GCTAACTTGTCAGTACTCTTTGGGAATCCTGGGATGGCTCTAGCGCTTCCGCAGCCGTTCCGCAGACGGGATAGATTTCACGATTTGCTTTTTTTTTTGTTTGCCGCCTAGGTTTTTGTTTGCGTT : 1521

Trip5-Hind  : TTTTTTTTATTCCGTATATGCCGTCCGTCCGTCTGGTAGATCGTGCTGCTACTTACGTTACGTTGTCACTTGTTGTCGGGTCATTGTTTGTCGGGTCATTGTTTGTCGGGTCATTTGTCATGTTTTTTGTTGTGATGATGTGGTCTGATTGGG : 1638
Trip5B-Hin  : TTTTTTTTATTCCGTATATGCCGTCCGTCCGTCTGGTAGATCGTGCTGCTACTTACGTTACGTTGTCACTTGTTGTCGGGTCATTGTTTGTCGGGTCATTGTTTGTCGGGTCATTTGTCATGTTTTTTGTTGTGATGATGTGGTCTGATTGGG : 1638
Trip5C-Hin  : TTTTTTTTATTCCGTATATGCCGTCCGTCCGTCTGGTAGATCGTGCTGCTACTTACGTTACGTTGTCACTTGTTGTCGGGTCATTGTTTGTCGGGTCATTGTTTGTCGGGTCATTTGTCATGTTTTTTGTTGTGATGATGTGGTCTGATTGGG : 1638
Trp5_varie  : TTTTTTTTATTCCGTATATGCCGTCCGTCCGTCTGGTAGATCGTGCTGCTACTTACGTTACGTTGTCACTTGTTGTCGGGTCATTGTTTGTCGGGTCATTGTTTGTCGGGTCATTTGTCATGTTTTTTGTTGTGATGATGTGGTCTGATTGGG : 1638

Trip5-Hind  : CTGTCGTTCTAGATCGGAGTAGAATAATGTGTCAAACTACCTCGTAGATTTTTTAAAAAAAATTCGGATTTGTATGTGTCATACATCTTCATAGTTAAGAACTTAAGATGA : 1755
Trip5B-Hin  : CTGTCGTTCTAGATCGGAGTAGAATAATGTGTCAAACTACCTCGTAGATTTTTTAAAAAAAATTCGGATTTGTATGTGTCATACATCTTCATAGTTAAGAACTTAAGATGA : 1755
Trip5C-Hin  : CTGTCGTTCTAGATCGGAGTAGAATAATGTGTCAAACTACCTCGTAGATTTTTTAAAAAAAATTCGGATTTGTATGTGTCATACATCTTCATAGTTAAGAACTTAAGATGA : 1755
Trp5_varie  : CTGTCGTTCTAGATCGGAGTAGAATAATGTGTCAAACTACCTCGTAGATTTTTTAAAAAAAATTCGGATTTGTATGTGTCATACATCTTCATAGTTAAGAACTTAAGATGA : 1755
```

FIG. 5C

```
                  1760         *         1780         *         1800         *         1820         *         1840         *         1860         *
Trip5-Hind : TGGATGGAAATATCGATCTTTAGATAAGGATAGGTATACATGTCGATGTGGGTTTAACTGGTACCTCGGTAGATGTATTGCTCTAACATGCTTTAGATGATGGCATATGCAGCATCT : 1872
Trip5B-Hin : TGGATGGAAATATCGATCTTTAGATAAGGATAGGTATACATGTCGATGTGGGTTTAACTGGTACCTCGGTAGATGTATTGCTCTAACATGCTTTAGATGATGGCATATGCAGCATCT : 1872
Trip5C-Hin : TGGATGGAAATATCGATCTTTAGATAAGGATAGGTATACATGTCGATGTGGGTTTAACTGGTACCTCGGTAGATGTATTGCTCTAACATGCTTTAGATGATGGCATATGCAGCATCT : 1872
Trp5_varie : TGGATGGAAATATCGATCTTTAGATAAGGATAGGTATACATGTCGATGTGGGTTTAACTGGTACCTCGGTAGATGTATTGCTCTAACATGCTTTAGATGATGGCATATGCAGCATCT : 1872

1880         *         1900         *         1920         *         1940         *         1960         *         1980
Trip5-Hind : GTTCATATGCTCTAACATGCTCTAACCTTGAGTACCTATCTATCTATCTATCTGAGTACCTATCATAATAAACAAGTATGTTTATAATTATTTGATCTTGATACACTTGGATGATGATGTATGCAGCAGCTATGTC : 1989
Trip5B-Hin : GTTCATATGCTCTAACATGCTCTAACCTTGAGTACCTATCTATCTATCTATCTGAGTACCTATCATAATAAACAAGTATGTTTATAATTACTTGATCTTGATACTTGGATGATGATGTATGCAGCAGCTATGTC : 1989
Trip5C-Hin : GTTCATATGCTCTAACATGCTCTAACCTTGAGTACCTATCTATCTATCTATCTGAGTACCTATCATAATAAACAAGTATGTTTATAATTATTTGATCTTGATACTTGGATGATGATGTATGCAGCAGCTATGTC : 1989
Trp5_varie : GTTCATATGCTCTAACATGCTCTAACCTTGAGTACCTATCTATCTATCTATCTGAGTACCTATCATAATAAACAAGTATGTTTATAATTATTTGATCTTGATACACTTGGATGATGATGTATGCAGCAGCTATGTC : 1989

2000         *         2020         *         2040         *         2060         *
Trip5-Hind : TTGATTTTTGCCCTGCCTTCATGTGCTGTTTATTTGCTGGGACTGTTCTTTTCTTTGTTGATGCTCACCCTGTTGGTGTTCCTTCTGCAG : 2077
Trip5B-Hin : TTGATTTTTGCCCTGCCTTCATGTGCTGTTTATTTGCTGGGACTGTTCTTTTCTTTGTTGATGCTCACCCTGTTGGTGTTCCTTCTTGCCAG : 2077
Trip5C-Hin : TTGATTTTTGCCCTGCCTTCATGTGCTGTTTATTTGCTGGGACTGTTCTTTTCTTTGTTGATGCTCACCCTGTTGGTGTTCCTTTTGCAG : 2077
Trp5_varie : TTGATTTTTGCCCTGCCTTCATGTGCTGTTTATTTGCTGGGACTGTTCTTTTCTTTGTTGATGCTCACCCTGTTGGTGTTCCTTGGTCAG : 2077
```

CIS-ACTING REGULATORY ELEMENTS FROM *TRIPSACUM DACTYLOIDES*

CROSS REFERENCE TO RELATED APPLICATION

This application claims the benefit of U.S. Provisional Application Ser. No. 60/662,293, filed Mar. 16, 2005, the contents of which are herein incorporated by reference in their entirety.

FIELD OF THE INVENTION

The present invention relates to the field of plant molecular biology, more particularly to the identification and use of regulatory elements in plants.

BACKGROUND OF THE INVENTION

Currently, there is a high demand for transgenic plants that express biotechnologically important protein products at a high or inducible level. Cis-acting sequences from viruses such as CMV have been used successfully in plants to drive expression of various genes. However, these sequences are often prone to rearrangement within the plant cell, and thus exhibit genetic instability. Furthermore, plant mechanisms of gene silencing often reduce, eliminate, or otherwise alter the expression of genes regulated by viral cis-acting elements, reducing the usefulness of such elements.

Ubiquitin is one of the most highly conserved proteins in eukaryotes and can be found throughout the plant body. Many polyubiquitin genes are expressed constitutively (Kawalleck et al. (1993) *Plant Mol. Biol.* 21:673-684), whereas others are expressed in a tissue-preferred manner (Callis and Bedinger (1994) *Proc. Natl. Acad. Sci. U.S.A.* 91:6074-6077; Plesse et al. (1997) *Mol. Gen. Genet.* 254:258-266), or are induced in response to environmental signals (Christensen and Quail (1989) *Plant Mol. Biol.* 12:619-632; Liu et al. (1995) *Biochem. Cell Biol.* 73:19-30).

Promoters from ubiquitin have been shown to drive reporter gene expression in transformed cells and plants. These promoters have been isolated from *Arabidopsis thaliana* (Callis et al. (1990) *J. Biol. Chem.* 265:12486-12493), sunflower (Binet et al. (1991) *Plant Sci.* 79:87-94), tobacco (Genschick et al. (1994) *Gene* 148:195-202; Plesse et al. (1997) *Mol. Gen. Genet.* 254:258-266), and maize (Christensen et al. (1992) *Plant Mol. Biol.* 18:675-689).

Maize ubiquitin promoter-based vectors have been developed which result in high-level expression of foreign genes in a number of monocots, including rice, wheat, sugarcane, maize, barley, *Pennisetum, Panicum,* and *Lemna* (Christensen and Quail (1996) *Transgenic Research* 5:213-218; U.S. Pat. Nos. 5,510,474; 5,614,399; 6,020,190; and 6,054,574), including expression of an herbicide resistance gene in rice (Toki et al. (1992) *Plant Physiol.* 100:1503-1507). A polyubiquitin promoter from potato (*Solanum tuberosum*) has been isolated and fusion transgenes with this promoter were introduced back into potato, resulting in constitutive production of the transgene in tuber peel, and inducible expression in tuber tissue and leaves (Garbarino et al. (1995) *Plant Physiol.* 109:1371-1378). In addition, rice polyubiquitin promoters have been shown to drive strong constitutive expression in transformed rice plants (U.S. Pat. No. 6,528,701; Wang et al. (2000) *Plant Sci.* 156:201-211).

The identification and isolation of regulatory elements useful for strong or inducible expression of genes in microorganisms and plants would be beneficial in the development of commercial varieties of transgenic plants.

SUMMARY OF INVENTION

Compositions and methods for regulating gene expression in a plant are provided. Compositions comprise a novel nucleotide sequence from *Tripsacum dactyloides* and variants thereof that initiate transcription in a plant. Specifically, a transcriptional initiation region isolated from a polyubiquitin gene of *Tripsacum dactyloides* is provided. Further compositions of the invention comprise the nucleotide sequences set forth in SEQ ID NOS:1, 2, 3, 5, and 6, the plant promoter sequence deposited in a bacterial host as Accession No. NRRL B-30819, and variants and fragments thereof. Compositions of the present invention also include expression cassettes comprising a promoter of the invention operably linked to a heterologous nucleotide sequence of interest. The invention further provides vectors comprising the expression cassettes, and plants and plant cells having stably incorporated into their genomes an expression cassette described above. Additionally, compositions include transgenic seed of such plants.

Methods are provided for expressing a nucleotide sequence in a plant or plant cell, as well as methods for identifying regulatory sequences, including promoters, transcriptional terminators or enhancers, or polyadenylation signals for use in a plant.

Operably linked to the promoter is a sequence of interest that may modify the phenotype of the plant. Such modification may include, for example, modulating the production of an endogenous product, or it may include production of an exogenous expression product to provide for a novel function or product in the plant. For example, a heterologous nucleotide sequence that encodes a gene product that confers herbicide or pest resistance is encompassed.

DESCRIPTION OF FIGURES

FIG. 1 shows the nucleotide sequence of the *Tripsacum dactyloides* ubiquitin promoter (SEQ ID NO:1). The PCR primer target regions used to amplify the fragment are underlined, the predicted transcription start site is shown in bold face, and the predicted intron is shown in lower case.

FIG. 2 shows the nucleotide sequence of a functional TripPro5 promoter region that is a fragment of SEQ ID NO:1 (SEQ ID NO:2). It contains Hind III and Pst I restriction sites. The Hind III and Pst I restriction sites are underlined, the predicted transcription start site is shown in bold face and the predicted intron is shown in lower case.

FIG. 3 shows the nucleotide sequence of a functional variant of the TripPro5 promoter of SEQ ID NO:2 (SEQ ID NO:3). The predicted transcription start site is shown in bold face and the predicted intron is shown in lower case.

FIGS. 4A and 4B show an alignment of the TripPro5 promoter region (SEQ ID NO:2) with the 5' flanking region of the maize polyubiquitin gene MubG1 (SEQ ID NO:4). Regions of nucleotide homology are shown in reverse text.

Figure 5A:
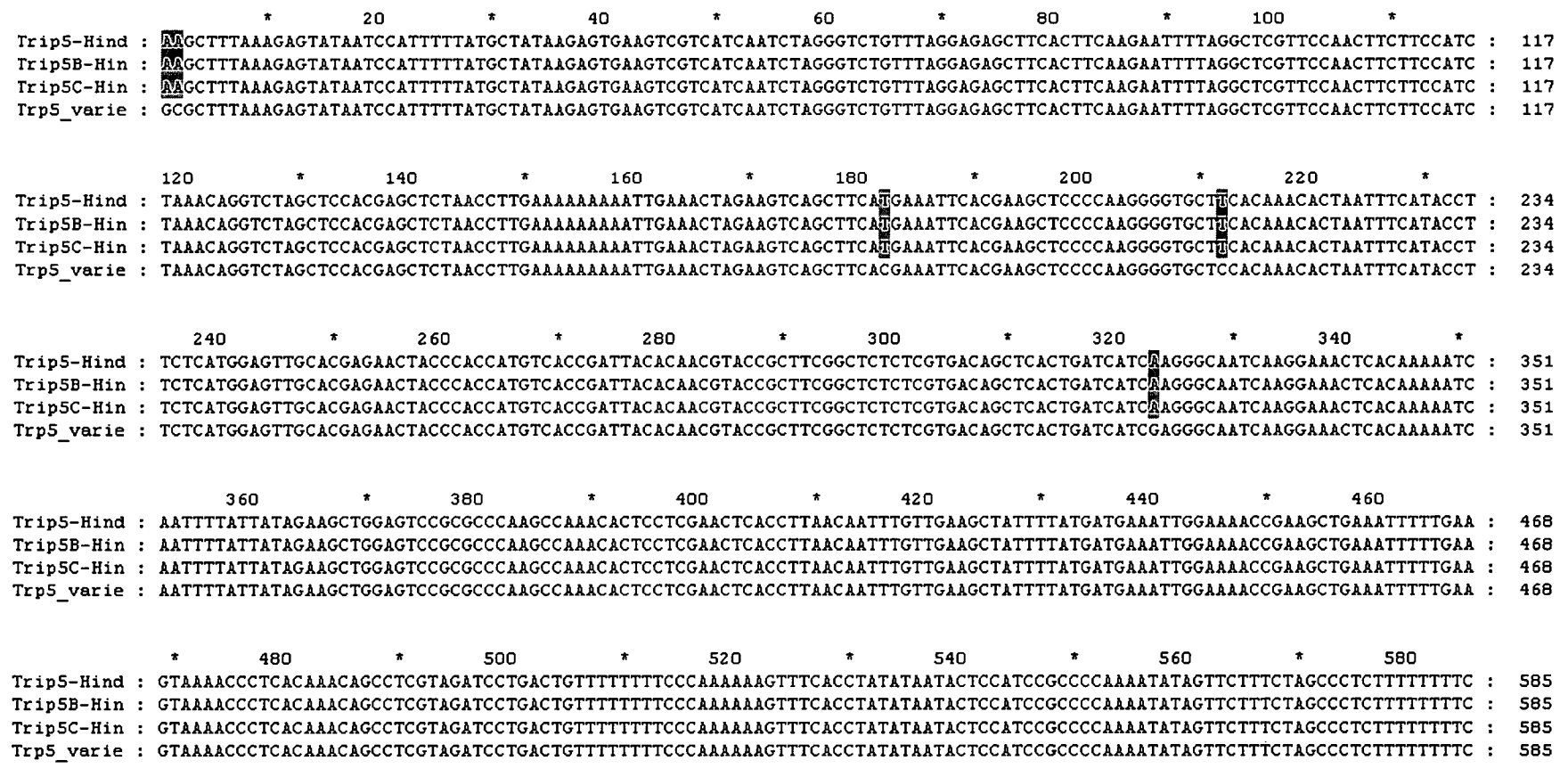
Figure 5B:
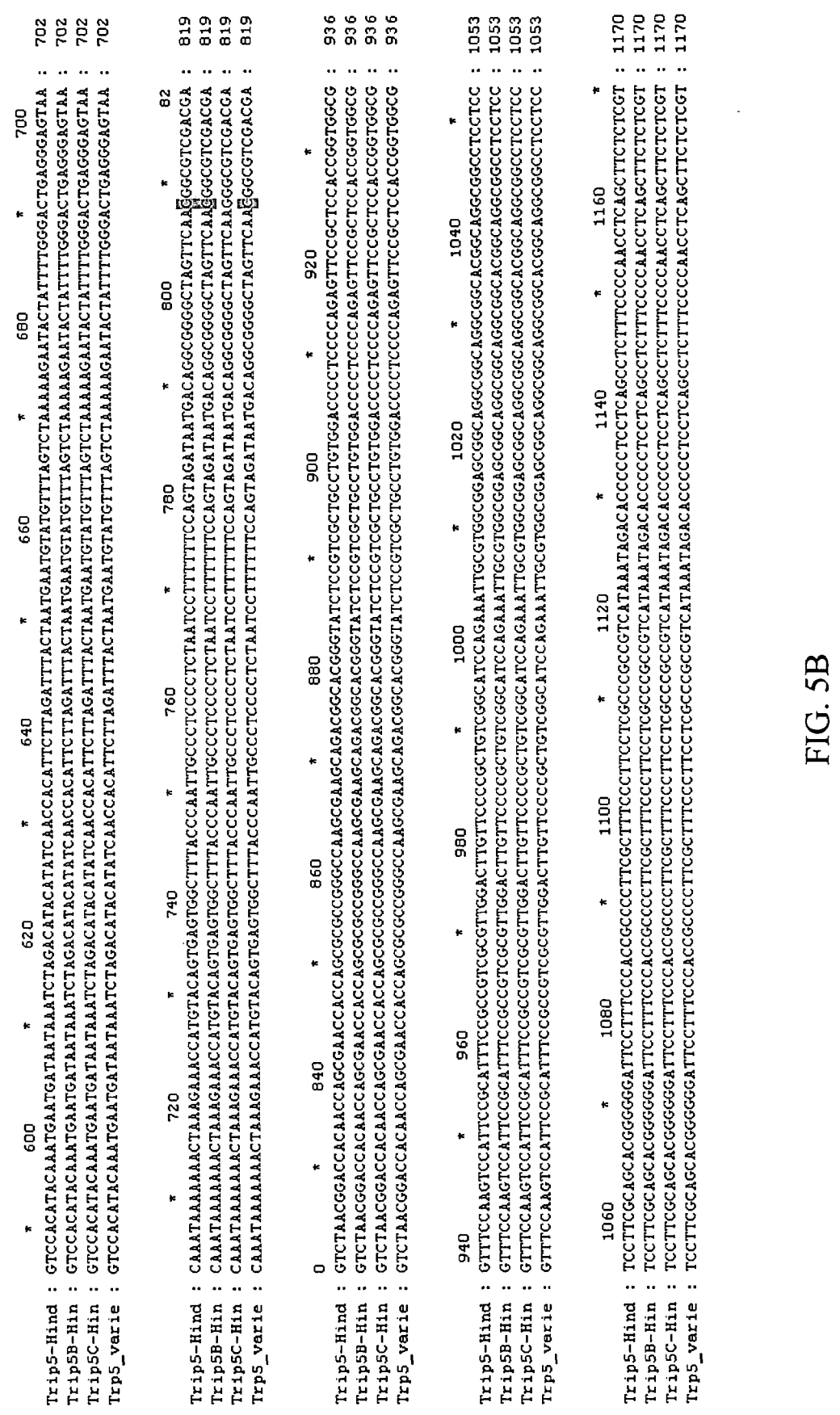

FIGS. 5A-5D show an alignment of the TripPro5 promoter region (SEQ ID NO:2) with the functional variants TripPro5B (SEQ ID NO:5), TripPro5C (SEQ ID NO:6) and TripPro5-Variant (SED ID NO:3). The shaded regions highlight the alterations in the nucleotide sequence of each variant with respect to TripPro5 (SEQ ID NO:2).

DETAILED DESCRIPTION

The present invention is drawn to compositions and methods for regulating gene expression in plants or plant cells. The compositions of the present invention comprise novel nucleotide sequences for the *Tripsacum dactyloides* ubiquitin promoter. In particular, the present invention provides for isolated promoter nucleic acid molecules comprising the nucleotide sequence set forth in SEQ ID NO:1, 2, 3, 5 or 6, plant promoter sequences deposited in bacterial hosts as Accession No. NRRL B-30819, and fragments and variants thereof. In addition, transformed plants, plant cells, and seeds are provided.

Plasmids containing the herbicide resistance nucleotide sequences of the invention were deposited in the permanent collection of the Agricultural Research Service Culture Collection, Northern Regional Research Laboratory (NRRL), 1815 North University Street, Peoria, Ill. 61604, United States of America, on Feb. 8, 2005, and assigned Accession No. NRRL B-30819. This deposit will be maintained under the terms of the Budapest Treaty on the International Recognition of the Deposit of Microorganisms for the Purposes of Patent Procedure. Access to these deposits will be available during the pendency of the application to the Commissioner of Patents and Trademarks and persons determined by the Commissioner to be entitled thereto upon request. Upon allowance of any claims in the application, the Applicants will make available to the public, pursuant to 37 C.F.R. § 1.808, sample(s) of the deposit with the ATCC. This deposit was made merely as a convenience for those of skill in the art and is not an admission that a deposit is required under 35 U.S.C. §112.

The promoter sequences of the invention, when assembled within a DNA construct such that the promoter is operably linked to a nucleotide sequence of interest, drive expression of the nucleotide sequence in the cells of an organism stably transformed with this DNA construct, particularly plant cells. The promoter sequences are also useful as probes for the isolation of other ubiquitin-like promoter sequences or genes, as molecular markers, and the like.

Methods for expressing a nucleotide sequence in a plant comprise introducing into plant cells an expression cassette comprising a promoter of the invention operably-linked to a nucleotide sequence of interest, and regenerating a transformed plant from the plant cell.

The articles "a" and "an" are used herein to refer to one or more than one (i.e., to at least one) of the grammatical object of the article. By way of example, "an element" means one or more elements.

As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "purified" nucleic acid molecule, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the promoter molecule can contain less than about 5 kb, 4 kb, 3 kb, 2 kb, 1 kb, 0.5 kb, or 0.1 kb of nucleotide sequence that naturally flanks the nucleic acid molecule in genomic DNA of the cell from which the nucleic acid is derived. Various aspects of the invention are described in further detail in the following subsections.

Isolated Nucleic Acid Molecules, and Variants and Fragments Thereof

Nucleotide sequences of the present invention include the promoter sequences set forth in SEQ ID NOS:1, 2, 3, 5 and 6, and variants thereof. By "promoter" is intended a nucleic acid sequence that functions to direct transcription of a downstream coding sequence. A promoter generally comprises a DNA sequence homologous to the consensus 5'-TATAAT-3' (TATA box) about 10-30 base pairs 5' to the transcription start (cap) site that is capable of directing RNA polymerase to initiate RNA synthesis. Promoters may further comprise other recognition sequences, generally upstream or 5' to the TATA box, referred to as upstream promoter elements, which influence the transcription initiation rate. These include the CAAT box, which is often found about 30 to 70 base pairs 5' to the TATA box and has homology to the canonical form 5'-CCAAT-3' (Breathnach and Chambon (1981) *Ann. Rev. Biochem.* 50:349-383). In plants the CAAT box is sometimes replaced by a sequence known as the AGGA box, a region having adenine residues symmetrically flanking the triplet G(orT)NG (Messing et al. (1983), in *Genetic Engineering of Plants*, T. Kosuge, C. Meredith and A. Hollaender (eds.), Plenum Press, New York, pp. 211-227). These elements, together with other transcriptional and translational regulatory nucleic acid sequences (also termed "control sequences"), are necessary for the expression of a DNA sequence of interest. Methods for isolating and identifying regulatory elements not described herein, such as enhancers and elements responsible for tissue or temporal expression of the coding region, are well known in the art. See, for example U.S. Pat. Nos. 5,635,618; 6,218,140; 6,303,370; 6,310,197; and 6,355,864.

By "core promoter" is intended a promoter without promoter elements. A core promoter contains essential nucleotide sequences for promoter function, including the TATA box and the initiation site of transcription. Such a region is normally present, with some variation, in most promoters. The core promoter region is often referred to as a minimal promoter region because it is functional on its own to promote a basal level of transcription.

Nucleic acid molecules that are fragments of the disclosed promoter sequences are also encompassed by the present invention. By "fragment" is intended a portion of the promoter sequence. A fragment of a nucleotide sequence may be biologically active and hence be capable of initiating transcription of an operably-linked nucleotide sequence in a plant, or it may be a fragment that can be used as a hybridization probe or PCR primer using methods disclosed below. Assays to determine whether such fragments decrease expression levels or alter the nature of expression, i.e., constitutive or inducible expression are well known in the art.

Nucleic acid molecules that are fragments of a promoter sequence may comprise at least about 20, 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500 contiguous nucleotides, or up to the number of nucleotides present in a full-length promoter sequence disclosed herein (for example, 2622 nucleotides for SEQ ID NO:1) depending upon the intended use. By "contiguous" nucleotides is intended nucleic acid residues that are immediately adjacent to one another. Biologically active fragments of the promoters of the present invention will retain promoter activity (i.e., initiating transcription). By "retains promoter activity" is intended that the fragment will have at least about 30%, at least about 50%, at least about 70%, or at least about 80% of the promoter activity of the full-length promoter. A biologically active portion of a promoter can be prepared by isolating a portion of one of the promoter nucleotide sequences of the invention and assessing the activity of that portion of the promoter. Methods for measuring promoter activity are well known in the art. See the section entitled "Evaluation of Promoter Activity" for examples of suitable methods.

Such fragments will generally comprise the TATA recognition sequence of the particular promoter sequence. These fragments may be obtained by cleaving the naturally occurring promoter nucleotide sequence disclosed herein with restriction enzymes, by synthesizing a nucleotide sequence from the naturally occurring sequence of the promoter DNA sequence, or through the use of PCR technology. See particularly, Mullis et al. (1987) *Methods Enzymol.* 155:335-350, and Erlich, ed. (1989) *PCR Technology* (Stockton Press, New York). For example, fragments of the promoter described in SEQ ID NO:1 include the 2077, 2077, 2083 and 2086 base pair promoters described in SEQ ID NOS:2, 3, 5 and 6, respectively. Variants of these promoter fragments, such as those resulting from site-directed mutagenesis, are also encompassed by the compositions of the present invention.

Variants of the promoter sequences disclosed herein are also encompassed. By "variant" is intended a sufficiently identical sequence. Promoter sequences encompassed by the present invention are sufficiently identical to the nucleotide sequence of SEQ ID NO:1, 2, 3, 5 or 6. By "sufficiently identical" is intended a nucleotide sequence that has at least about 70% or 75%, about 80% or 85% sequence identity, about 90%, 91%, 92%, 93%, 94%, 95%, 96%, 97%, 98% or 99% sequence identity compared to a reference sequence using one of the alignment programs as described herein.

Naturally occurring variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still have promoter activity as defined herein.

Variants encompassed by the present invention are biologically active, that is they continue to possess the desired biological activity of the native sequence, that is, retaining promoter activity (i.e., initiating transcription). For example, biologically active variants of SEQ ID NOS:1 and 2 are described in SEQ ID NOS:3, 5 and 6. By "retains promoter activity" is intended that the variant will have at least about 30%, at least about 50%, at least about 70%, or at least about 80% of the promoter activity of the native sequence. Methods for measuring promoter activity are well known in the art. See the section entitled "Evaluation of Promoter Activity" for examples of suitable methods.

The skilled artisan will further appreciate that changes can be introduced by mutation into the nucleotide sequences of the invention without altering the ability of the promoter to drive expression in a plant cell. Thus, variant isolated nucleic acid molecules can be created by introducing one or more nucleotide substitutions, additions, or deletions into the corresponding nucleotide sequence disclosed herein. Mutations can be introduced by standard techniques, such as site-directed mutagenesis and PCR-mediated mutagenesis. Such variant nucleotide sequences are also encompassed by the present invention.

Alternatively, variant nucleotide sequences can be made by introducing mutations randomly along all or part of the promoter sequence, such as by saturation mutagenesis, and the resultant mutants can be screened for ability to drive expression of an operably linked nucleotide sequence in a plant cell.

By "operably linked" is intended a functional linkage between a promoter and a second sequence, wherein the promoter sequence initiates and mediates transcription of the DNA sequence corresponding to the second sequence. Generally, but not always, operably linked means that the nucleic acid sequences being linked are contiguous and, where necessary to join two protein coding regions, contiguous and in the same reading frame.

To determine the percent identity of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN program of Altschul et al. (1990) *J. Mol. Biol.* 215:403. BLAST nucleotide searches can be performed with the BLASTN program, score=100, wordlength=12, to obtain nucleotide sequences homologous to promoters of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTN) can be used. See, www.ncbi.nlm.nih.gov. Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the DNA sequence, and thus can provide data about the sequence conservation of the entire nucleotide sequence. The ClustalW algorithm is used in several commercially available DNA analysis software packages, such as the ALIGNX module of the vector NTi Program Suite (Informax, Inc). A non-limiting example of a software program useful for analysis of ClustalW alignments is GeneDoc™. Genedoc™ (Karl Nicholas) allows assessment of DNA similarity and identity between multiple genes. Another preferred, non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., 9865 Scranton Rd., San Diego, Calif., USA).

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

Using methods such as PCR, hybridization, and the like, corresponding sequences from other organisms, particularly other plants, can be identified, such sequences having substantial identity to the sequences of the invention. See, for example, Sambrook J., and Russell, D. W. (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY). Sequences identified by their identity to the promoter sequences set forth herein are encompassed by the present invention.

Oligonucleotide primers can be designed for use in PCR reactions to amplify corresponding DNA sequences from cDNA or genomic DNA from a plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Cold Spring Harbor, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, and partially-mismatched primers.

In a hybridization method, all or part of a known nucleotide sequence can be used to screen cDNA or genomic libraries. Methods for construction of such cDNA and genomic libraries are generally known in the art and are disclosed in Sambrook and Russell, 2001, supra. The hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known promoter sequence disclosed herein. Degenerate primers designed on the basis of conserved nucleotides in the nucleotide sequence can additionally be used. The probe typically comprises a region of nucleotide sequence that hybridizes under stringent conditions to at least about 12, at least about 25, at least about 50, 75, 100, 125, 150, 175, 200, 250, 300, 350, or 400 consecutive nucleotides of the promoter sequence of the invention or a fragment or variant thereof. Preparation of probes for hybridization is generally known in the art and is disclosed in Sambrook and Russell, 2001, supra, herein incorporated by reference.

For example, the entire promoter sequence disclosed herein, or one or more portions thereof, may be used as a probe capable of specifically hybridizing to corresponding promoter-like sequences. To achieve specific hybridization under a variety of conditions, such probes include sequences that are unique and are at least about 10 nucleotides in length, or at least about 20 nucleotides in length. Such probes may be used to amplify corresponding promoter sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, or less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. Optionally, wash buffers may comprise about 0.1% to about 1% SDS.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6(log M)+0.41(% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), the SSC concentration can be increased so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated sequences that have promoter activity and which hybridize under stringent conditions to the promoter sequences disclosed herein, or to fragments thereof, are encompassed by the present invention.

Methods of Use

Methods of the present invention are directed to expressing heterologous nucleotide sequences in plants and plant cells under the control of the promoter sequence of the present invention. The transgenic plants may have a change in phenotype, including, but not limited to, an altered pathogen or insect defense mechanism, an increased resistance to one or more herbicides, an increased ability to withstand stressful environmental conditions, a modified ability to produce starch, a modified level of starch production, a modified oil content and/or composition, a modified ability to utilize, partition and/or store nitrogen, and the like. These results can be achieved through the expression of heterologous genes or by the increased expression of endogenous products in plants. Alternatively, the results can be achieved by reducing the expression of one or more endogenous products, particularly enzymes, transporters, or cofactors, or affecting nutrient uptake in the plant.

Generally, the nucleotide sequence for the promoter of the invention is provided in an expression cassette with a nucleotide sequence of interest, typically a heterologous nucleotide sequence, for expression in the plant of interest. By "heterologous nucleotide sequence" is intended a sequence that is not naturally operably-linked with the promoter sequence, including non-naturally occurring multiple copies of a naturally occurring DNA sequence. While this nucleotide sequence is heterologous to the promoter sequence, it may be homologous, or native, or heterologous, or foreign, to the plant host. It is recognized that the promoter may also drive expression of its homologous or native nucleotide sequence. In some cases, the transformed plant may have a change in phenotype. Heterologous nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

Any sequence of interest may be expressed by the promoter sequences of the invention. Such heterologous nucleotide sequences include, but are not limited to, herbicide-tolerance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, and oil content and/or composition.

More specific genes of interest for the present invention include, but are not limited to, genes that improve crop yield, genes that improve desirability of crops, genes encoding proteins conferring resistance to abiotic stress, such as drought, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms. It is recognized that any gene of interest can be operably linked to the promoter sequences of the invention and expressed in a plant.

These heterologous nucleotide sequences may encode proteins involved in providing disease or pest resistance. By "disease resistance" or "pest resistance" is intended that the plants avoid the harmful symptoms that are the outcome of the plant-pathogen interactions. Disease resistance and insect resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products. Examples of genes of interest may be found, for example, at www.nbiap.vt.edu/cfdocs/fieldtests2.cfm.

"Pest" includes, but is not limited to, insects, fungi, bacteria, viruses, nematodes, mites, ticks, and the like. Insect pests include insects selected from the orders *Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera*, etc., particularly *Coleoptera, Lepidoptera*, and *Diptera*. Viruses include but are not limited to tobacco or cucumber mosaic virus, ringspot virus, necrosis virus, maize dwarf mosaic virus, etc. Nematodes include but are not limited to parasitic nematodes such as root knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include but are not limited to *Pratylenchus* spp. Fungal pests include those that cause leaf, yellow, stripe and stem rusts.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS), in particular the sulfonylurea-type herbicides, genes coding for resistance to herbicides that act to inhibit the action of glutamine synthase, such as phosphinothricin or basta (e.g., the bar gene), glyphosate (e.g., the EPSP synthase gene and the GAT gene) or other such genes known in the art.

Genes that improve crop yield include dwarfing genes, such as Rht1 and Rht2 (Peng et al. (1999) *Nature* 400:256-261), and those that increase plant growth, such as ammonium-inducible glutamate dehydrogenase. Genes that improve desirability of crops include, for example, those that allow plants to have a reduced saturated fat content, those that boost the nutritional value of plants, and those that increase grain protein. Genes that improve salt tolerance are those that increase or allow plant growth in an environment of higher salinity than the native environment of the plant into which the salt-tolerant gene(s) has been introduced.

Methods for identifying regulatory elements (e.g., promoters, terminators and enhancers) are also provided. By "regulatory element" or "regulatory region" is intended a portion of nucleic acid found upstream or downstream of a gene, that may be comprised of either DNA or RNA, or both DNA and RNA and that is involved in gene expression. Regulatory elements may be capable of mediating organ specificity, or controlling developmental or temporal gene activation and include promoter elements, core promoter elements, elements that are inducible in response to an external stimulus, elements that are activated constitutively, transcriptional terminators, polyadenylation signals, and elements that decrease or increase promoter activity such as negative regulatory elements or transcriptional enhancers, respectively. By "cis-acting" is intended a sequence that is physically contiguous with the transcribed sequence. Cis-acting sequences typically interact with proteins or other molecules to carry out (turn on/off, regulate, modulate, etc.) transcription. By "transcriptional enhancer" is intended a nucleic acid sequence that, when positioned proximate to a promoter and present in a transcription medium capable of supporting transcription, confers increased transcription activity compared to that resulting from the promoter in the absence of the enhancer. Enhancers may function upstream, within, or downstream of a gene, even as far away as 50 kilobases from the transcriptional initiation site. Enhancers may also function independently of their orientation. By "transcriptional terminator" is intended a DNA sequence that includes a nucleotide base pair sequence necessary for reducing or eliminating transcription. By "polyadenylation signal" is intended a sequence that controls the termination of transcription and translation.

Regulatory sequences for use in plants may be cloned from *Tripsacum* by designing one or more PCR primers based on the sequence of a plant gene, or a regulatory element. Preferably, the plant is a monocot, such as maize. The method may comprise designing at least one primer capable of hybridizing to a nucleotide sequence from a plant, using the primer to amplify DNA from a *Tripsacum* species to create amplified DNA, and testing the amplified DNA for regulatory sequence activity. By "regulatory sequence activity" is intended the ability to effect the transcription or translation of a gene. It includes promoter activity, transcriptional enhancer activity, transcriptional termination activity, and polyadenylation activity. Methods to measure or test for promoter activity are well known in the art (see section entitled "Evaluation of Promoter Activity"). Methods to measure or test for enhancer activity are well known in the art (see, for example, U.S. Pat. Nos. 6,806,064, 6,818,757, and 6,784,289). Methods to measure or test for terminator activity are well known in the art (see, for example, U.S. Pat. No. 5,093,252). Methods to measure or test for polyadenylation activity are well known in the art (see, for example, U.S. Pat. No. 6,632,637).

Alternatively, regulatory elements may be identified and cloned by other approaches. For example, *Tripsacum* genomic or subgenomic libraries could be constructed using BAC, cosmid or lambda vectors. The libraries could be probed using promoter elements from a plant, such as maize or another monocot. Alternatively the libraries could be probed using gene coding regions from a plant, preferably maize or another monocot. The resulting clones could be sequenced and the cis-acting elements surrounding the *Tripsacum* coding regions determined. Alternatively, fragments from the coding regions of various *Tripsacum* genes could be amplified from genomic DNA by PCR using primers designed from conserved regions of plant genes, such as conserved regions from maize. The *Tripsacum* coding region fragments could then be used to probe genomic libraries as described.

Cis-acting elements could be cloned using inverse PCR. Sequence of *Tripsacum* gene coding regions could be obtained as described above, then PCR primers designed and inverse PCR used to clone DNA flanking the coding regions using techniques well known in the art.

Antisense

The heterologous nucleotide sequence that is operably linked to the *Tripsacum* polyubiquitin promoter disclosed herein may be an antisense nucleotide sequence for a targeted gene. By "antisense nucleotide sequence" is intended a sequence that is in inverse orientation to the 5'-to-3' normal orientation of that nucleotide sequence. Expression of an antisense DNA sequence in a plant cell prevents the normal expression of the targeted gene. The antisense nucleotide sequence encodes an RNA transcript that is complementary to and capable of hybridizing to the endogenous messenger RNA (mRNA) produced by transcription of the targeted gene. In this way, production of the native protein encoded by the targeted gene is inhibited and a desired phenotypic response is achieved. Modifications of the antisense sequences may be made as long as the sequences hybridize to and interfere with expression of the corresponding mRNA. Antisense constructions having about 70%, 80%, 85%, 90% or 95% sequence identity to the corresponding antisense sequences may be used. Furthermore, portions of the antisense nucleotides may be used to disrupt the expression of the target gene. Generally, sequences of at least 50 contiguous nucleotides, 100 contiguous nucleotides, 200 contiguous nucleotides, or greater may be used. Thus, the promoter sequences disclosed herein may be operably linked to antisense DNA sequences to reduce or inhibit expression of a native protein in the plant.

Plant Expression Cassettes and Transformation Vectors

Transformation of plant cells can be accomplished by one of several techniques known in the art. By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen). "Transgenic plants" or "transformed plants" or "stably transformed" plants or cells or tissues refer to plants that have incorporated or integrated exogenous nucleic acid sequences or DNA fragments into the plant cell. By "stable transformation" is intended that the nucleotide construct introduced into a plant integrates into the genome of the plant and is capable of being inherited by progeny thereof.

The promoter sequence of the invention may be provided in an expression cassette that allows it to drive expression of a heterologous sequence of interest in plant cells. By "expression cassette" is intended a DNA construct that is capable of resulting in the expression of a protein from an open reading frame in a cell. The cassette will include in the 5'-3' direction of transcription, a transcriptional initiation region comprising one of the promoter nucleotide sequences disclosed herein, or variants or fragments thereof, operably-linked to a heterologous sequence of interest, and a translational and transcriptional termination region (i.e., termination region) functional in plants. The cassette may additionally contain at least one additional gene to be cotransformed into the organism, such as a selectable marker gene. Alternatively, the additional gene(s) can be provided on multiple expression cassettes. Such an expression cassette is provided with a plurality of restriction sites for insertion of the heterologous sequence of interest to be under the transcriptional regulation of the regulatory regions.

Often, such constructs will also contain 5' and 3' untranslated regions. Such constructs may also contain a translated "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression. By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like.

By "3' untranslated region" is intended a nucleotide sequence located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a nucleotide sequence located upstream of a coding sequence. Other upstream or downstream untranslated elements include enhancers. Enhancers are nucleotide sequences that act to increase the expression of a promoter region. Enhancers are well known in the art and include, but are not limited to, the SV40 enhancer region and the 35S enhancer element.

The termination region may be native with the transcriptional initiation region comprising the promoter nucleotide sequence of the present invention, may be native with the DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) of interest may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are known in the art for synthesizing plant-preferred genes. See, for example, U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide or signal sequence to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Typically this "plant expression cassette" will be inserted into a "plant transformation vector." By "transformation vector" is intended a DNA molecule that is necessary for efficient transformation of a cell. Such a molecule may consist of one or more expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. By "introducing" is intended to present to the organism being transformed the nucleotide construct in such a manner that the construct gains access to the interior of at least one cell of the organism.

This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as 'binary vectors'. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication.

The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as in understood in the art (Hellens and Mullineaux (2000) *Trends in Plant Science*, 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grow into mature plant and produce fertile seeds (e.g. Hiei et al. (1994) *The Plant Journal* 6:271-282; Ishida et al. (1996) *Nature Biotechnology* 14:745-750). A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods may be used to confirm the presence of the integrated heterologous gene of interest in the genome of transgenic plant.

Generation of transgenic plants may be performed by one of several methods, including, but not limited to, introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Plants

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

This invention is particularly suitable for any member of the monocot plant family including, but not limited to, maize, rice, barley, oats, wheat, sorghum, rye, sugarcane, pineapple, yams, onion, banana, coconut, and dates.

Evaluation of Plant Transformation

Following introduction of heterologous foreign DNA into plant cells, the transformation or integration of heterologous DNA in the plant genome is confirmed by various methods such as analysis of nucleic acids or proteins and metabolites associated with the integrated DNA.

PCR analysis is a rapid method to screen transformed cells, tissue or shoots for the presence of incorporated DNA at the earlier stage before transplanting into the soil (Sambrook and Russell, 2001. *Molecular Cloning: A Laboratory Manual.* Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" then is probed with, for example, radiolabeled $^{32}$P target DNA fragment to confirm the integration of introduced DNA in the plant genome according to standard techniques (Sambrook and Russell, 2001, supra).

In Northern blot analysis, RNA is isolated from specific tissues of transformant, fractionated in a formaldehyde agarose gel, blotted onto a nylon filter according to standard procedures that are routinely used in the art (Sambrook and Russell, 2001, supra). Expression of RNA encoded by a heterologous gene operably linked to the TripPro5 promoter is then tested by hybridizing the filter to a radioactive probe derived from the heterologous gene, by methods known in the art (Sambrook and Russell, 2001, supra).

Evaluation of Promoter Activity

Numerous methods are available to assess promoter activity in plants. Promoter function during expression of a gene of interest under its regulatory control may be tested at either the transcriptional or translational stage. At the transcriptional stage, RNA levels may be tested by DNA-RNA hybridization assays (i.e., Northern blot analysis), competitive reverse transcriptase PCR and RNAse protection assays. At the translational stage promoter activity may be determined by using specific functional assays for the protein synthesized (for example, by enzymatic activity or by immunoassay of the protein). For example, reporter gene activity, such as β-glucuronidase activity, luciferase activity or GFP fluorescence may be monitored at various times after transformation. Reporter gene activity may be monitored by enzymatic activity, by staining cells or tissue with substrate for the enzyme encoded by the reporter gene or by direct visualization under an appropriate wavelength of light (see, for example, Wang et al. (2000) *Plant Science* 156:201-211). Western blot may be carried out on the transgenic plants to confirm the presence of protein encoded by a gene of interest operably linked to the TripPro5 promoter by standard procedures (Sambrook and Russell, 2001, supra) using antibodies that bind to one or more epitopes present on the protein. Full-length promoter sequences, deletions and mutations of the promoter sequence may be assayed and their expression levels compared. See, for example, U.S. Pat. No. 6,072,050; and Sambrook et al. (1989) *Molecular Cloning: A Laboratory Manual* (2d ed., Cold Spring Harbor Laboratory Press, Cold Spring Harbor, N.Y.), herein incorporated by reference.

The following examples are offered by way of illustration and not by way of limitation.

EXPERIMENTAL

Example 1

Isolation of Cis-Acting Elements

*Tripsacum dactyloides* plants were obtained from a commercial nursery and genomic DNA was extracted using methods well known in the art. PCR primers were designed to amplify the promoter region of a polyubiquitin gene using published sequences of maize genes (GENBANK® Accession No. U29159).

PCR was performed with the primers described above and *Tripsacum dactyloides* genomic DNA as the template. The resulting PCR products amplified from *Tripsacum* DNA were approximately the same size as fragments that would be amplified from maize DNA. This finding was unexpected since promoter regions as a rule are not highly conserved among species. Database comparisons and alignments demonstrated that the fragments were homologous to monocot polyubiquitin promoters. One fragment, contained in the plasmid pAX306, was chosen for further characterization. This fragment contains 32 base pairs of polyubiquitin coding region and approximately 2 kb of the 5' flanking sequence. The complete DNA sequence was determined and is presented in FIG. 1 (SEQ ID NO:1). The Hind III to Pst I restriction fragment from plasmid pAX306 containing 2077 bp of the *Tripsacum* ubiquitin 5' flanking DNA was used to construct plant gene expression vectors. The sequence of this fragment, designated TripPro5 (*Tripsacum* promoter number 5), is presented in SEQ ID NO:2. This promoter is also referred to herein as the Trp5 promoter.

Figure 4A:
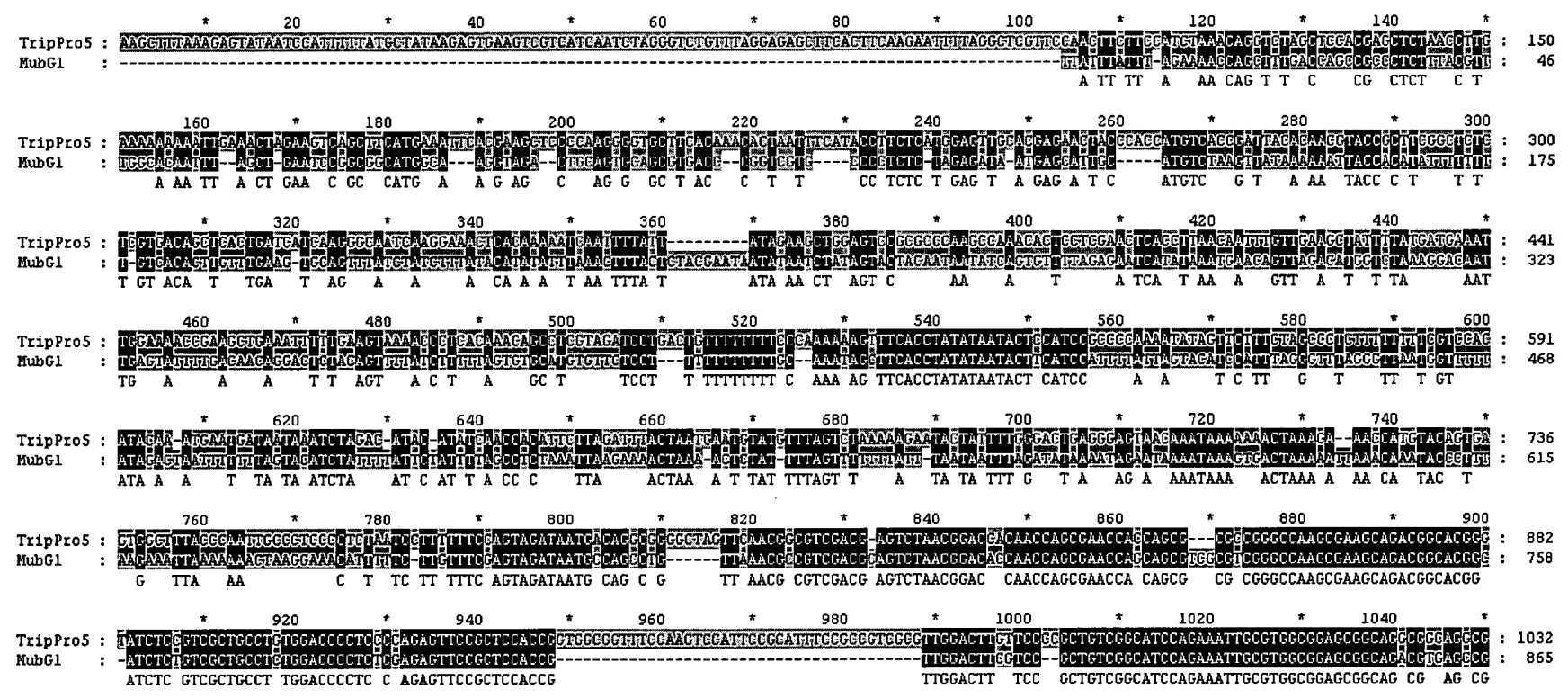
Figure 4B:
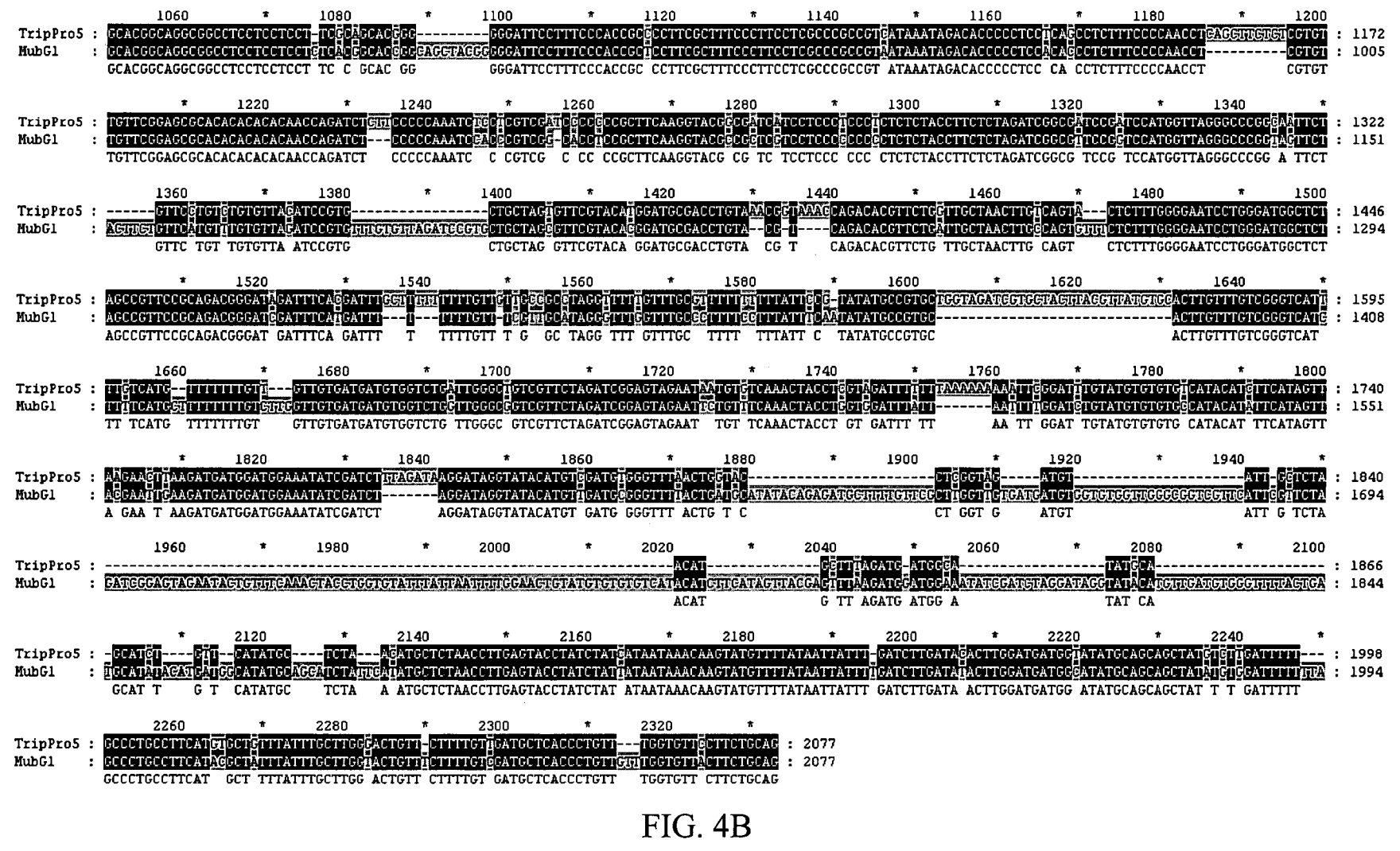

The 2077 bp TripPro5 promoter fragment sequence was aligned with the corresponding 2077 bp region of the maize polyubiquitin 5' flanking DNA (nucleotides 266-2342 of MubG1, GENBANK® Accession No. U29159)(SEQ ID NO:4) using the Clustal W alignment matrix (see FIG. 4). Overall nucleotide sequence identity to MubG1 is 59%.

Based on comparisons to the 5' flanking regions of other monocot polyubiquitin genes, the transcription start site is predicted to be at base 1147 of SEQ ID NO:2 and the 5' flanking region contains an intron consisting of bases 1244 to 2077.

Example 2

Construction of Vectors Using the TripPro5 Promoter

The 2077 bp HindIII to PstI restriction fragment containing TripPro5 was ligated into the plasmid vector pBluescriptII (Stratagene, La Jolla, Calif.). The PINII terminator (An et al. (1989) *Plant Cell* 1:115-122) was amplified from potato genomic DNA by PCR and ligated 3' to the TripPro5 fragment using methods well known in the art. The resulting plasmid was named pAX215 and contains a plant gene expression cassette comprising the TripPro5 promoter and PinII terminator.

Example 3

Expression of the Luciferase Reporter Gene

The luc+ gene encoding the reporter enzyme luciferase was amplified from the plasmid pGL3 basic (Promega Corp, Madison, Wis.) by PCR. Restriction sites were modified during PCR by methods well known in the art and the fragment was sequenced to ensure against PCR-induced errors. The luc+ reporter fragment was ligated between the TripPro5 promoter and PinII terminator to produce the plasmid pAX436. A similar plasmid, pAX418, was constructed using the rice actin promoter from pCOR113 (McElroy et al. (1991) *Mol. Gen. Genet.* 231:150-160), the luc+ gene, and the PinII terminator.

The plasmids pAX418 and pAX436 were transformed into immature maize embryos via aerosol beam injection as described in US Patent Application No. 20040219676 (PCT Publication No. WO 01/38514). Embryos were homogenized in GLO lysis buffer (Promega Corp.) 3, 7, or 14 days after transformation. Luciferase activity was analyzed using the Promega STEADY-GLO® Luciferase Assay System and a luminometer (Turner Designs 20/20, Sunnyvale, Calif.). Protein concentrations in the homogenates were determined using a Bio-Rad Protein Assay kit (Hercules, Calif.). Luciferase activity was normalized to protein concentration and the results are presented in Table 1.

TABLE 1

Relative light units per microgram protein

| Plasmid | Promoter | 3 days | 7 days | 14 days |
|---|---|---|---|---|
| pAX418 | Rice Actin | 14.6 | 5.4 | 0.10 |
| pAX436 | TripPro5 | 19.2 | 6.4 | 0.24 |
| none | — | 0.0001 | 0.0002 | 0.00004 |

Example 4

Expression of Luciferase in Maize Plant Cells by TripPro5

A plasmid designed to express luciferase driven by the TripPro5 promoter was designed and built as follows: pAX436 was digested with the restriction enzymes Hind III and Pac I, and the fragment (containing the TripPro5 promoter fused to the 5' end of the luciferase gene) isolated by gel-purification from an agarose gel as known in the art. Separately, plasmid pAX541 was digested with the restriction enzymes Hind III and Pac I, and the portion of the vector lacking a promoter as well as the 5' end of luciferase was isolated by gel-purification from an agarose gel as known in the art. The two fragments were ligated as known in the art, and the resulting confirmed plasmid was designated pAX543. pAX543 contains the luciferase gene immediately downstream from the TripPro5 promoter, such that expression of transcript from TripPro5 would be expected to result in expression of luciferase protein.

pAX543 was transformed into *Agrobacterium*, and stable *Agrobacterium* lines containing pAX543 integrated into the pSB1 plasmid were isolated by antibiotic selection as known in the art. The resulting *Agrobacterium* strain was designated pAG543.

pAG543 was used to infect maize callus cells as known in the art, and trangenic maize lines containing the TripPro5/Luciferase/terminator region of pAG543 were isolated, and confirmed by PCR analysis. Two plant lines were tested for the ability to express luciferase due to the activity of the TripPro promoter. Leaf cuttings of transgenic plants were sprayed with luciferin substrate, and in both cases, strong luminescence due to luciferase activity was observed.

Example 5

Trp5-Variant: A Functional Variant of the TripPro5 Promoter

The TripPro5 promoter of SEQ ID NO:2 was altered by PCR-based techniques as known in the art in order to destroy the Pst I restriction site present at the 3' terminus of the promoter, adjacent to the 3' acceptor of the TripPro5 intron. The resulting sequence (SEQ ID NO:3) contains a two nucleotide alteration of the Pst I site from CTGCAG to CGTCAG, and is immediately followed by the sequence ACTAGT, which adds an Spe I restriction site to facilitate cloning of genes to be driven by the promoter. This promoter is referred to as TripPro5-Variant or "Trp5-Variant." As a consequence of PCR amplification and cloning, TripPro5-Variant contains a several base change in the promoter relative to SEQ ID NO:2: (1) an A to G change at position 1, (2) an A to C change at position 2 (3) a T to C change at position 182, (4) a T to C change at position 212, (5) an A to G change at position 323. By "position" is intended the nucleotide position corresponding to that which is listed in SEQ ID NO:2. The nucleotide changes are summarized in Table 2 below.

TABLE 2

Nucleotide changes in variant sequence

| Position corresponding to SEQ ID NO: 2 | TripPro5 | TripPro5-Variant |
|---|---|---|
| 1 | A | G |
| 2 | A | C |
| 182 | T | C |
| 212 | T | C |
| 323 | A | G |
| 2073 | T | G |
| 2074 | G | T |

The TripPro5-Variant promoter was tested for activity with a heterologous gene of interest and found to be active in maize cells. The TripPro5-Variant promoter was tested by engineering a construct that contains (1) the Variant promoter (2) a gene immediately downstream of the promoter organized to allow expression of the open reading frame, and (3) a DNA element containing a 3' untranslated region and transcriptional terminator. Transgenic plants containing this construct were generated. The TripPro5-Variant promoter led to the expression of the correct protein from the open reading frame in maize cells.

Example 6

TripPro5B: A Functional Variant of the TripPro5 Promoter

The TripPro5 promoter of SEQ ID NO:2 was altered by PCR-based techniques as known in the art in order to destroy the Pst I restriction site present at the 3' terminus of the promoter, adjacent to the 3' acceptor of the TripPro5 intron. The resulting sequence (SEQ ID NO:5) contains a change of the Pst I site from CTGCAG to TTGCAG, and is immediately followed by the sequence GGATTCC, which adds a BamH I restriction site to facilitate cloning of genes to be driven by the promoter. This promoter is referred to as TripPro5B or Trp5B. As a consequence of PCR amplification and cloning, TripPro5B contains an additional base change from C to G at position 1378 corresponding to SEQ ID NO:2 (summarized in Table 3)

TABLE 3

Nucleotide changes in variant sequence

| Position | TripPro5 | TripPro5B |
|---|---|---|
| 1378 | A | G |
| 2072 | C | T |

The TripPro5B promoter was tested for activity with a heterologous gene of interest and found to be active in maize cells. TripPro5B was tested by engineering a construct that contains (1) the TripPro5B promoter, (2) a gene immediately downstream of the promoter organized to allow expression of the open reading frame, and (3) a DNA element containing a 3' untranslated region and transcriptional terminator. Transgenic plants containing this construct were generated. TripPro5B was found to cause expression of the correct protein from the open reading frame in maize cells.

Example 7

TripPro5C: A Functional Variant of the TripPro5 Promoter

The TripPro5 promoter of SEQ ID NO:2 was altered by PCR-based techniques as known in the art in order to destroy the Pst I restriction site present at the 3' terminus of the promoter, adjacent to the 3' acceptor of the TripPro5 intron. The resulting sequence (SEQ ID NO:6) contains a change of the Pst I site from CTGCAG to TTGCAG and is immediately followed by the sequence GACTAGT, which adds an Spe I restriction site to facilitate cloning of genes to be driven by the promoter. This promoter is referred to as TripPro5C or Trp5C. As a consequence of PCR amplification and cloning, TripPro5C contains an additional base change from C to G at position 808 corresponding to SEQ ID NO:2 (summarized in Table 4).

TABLE 4

Nucleotide changes in variant sequence

| Position | TripPro5 | TripPro5C |
|---|---|---|
| 808 | C | G |
| 2072 | C | T |

The TripPro5C promoter was tested for activity with a heterologous gene of interest and found to be active in maize cells. TripPro5C was tested by engineering a construct that contains (1) the TripPro5C promoter, (2) a gene immediately downstream of the promoter organized to allow expression of the open reading frame, and (3) a DNA element containing a 3' untranslated region and transcriptional terminator. Transgenic plants containing this construct were generated. TripPro5C was found to cause expression of the correct protein from the open reading frame in maize cells.

Example 8

Engineering Genes for Expression from TripPro5 and Variants Thereof

DNA expression constructs using the promoters described herein can be engineered in the following manner. It is recognized that any number of methods, such as those described elsewhere herein or well known in the art, can be employed to utilize these promoters and are so encompassed by this invention.

For the TripPro5 promoter, DNA expression constructs may be organized such that the promoter sequence of SEQ ID NO:2 is immediately followed by the sequence ACCATG, where the sequence ATG is the start codon of the gene to be expressed.

For the TripPro5-Variant Promoter, DNA expression constructs may be organized such that the promoter sequence of SEQ ID NO:3 is immediately followed by the sequence CCACCATG, where the underlined sequence ATG is the start codon of the gene to be expressed.

For Trp5B, DNA expression constructs may be organized such that the promoter sequence of SEQ ID NO:5 is immediately followed by the sequence ACCATG, where the underlined sequence ATG is the start codon of the gene to be expressed.

For Trp5C, DNA expression constructs may be organized such that the promoter sequence of SEQ ID NO:6 is immediately followed by the sequence CCACCATG, where the underlined sequence ATG is the start codon of the gene to be expressed.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

---

That which is claimed:

1. An isolated nucleic acid molecule comprising a nucleotide sequence having at least 99% sequence identity to the sequence set forth in SEQ ID NO:2, wherein said nucleotide sequence initiates transcription in a plant cell.

2. An expression cassette comprising the nucleotide sequence of claim 1 operably linked to a heterologous nucleotide sequence of interest.

3. A vector comprising the expression cassette of claim 2.

4. A plant cell having stably incorporated into its genome the expression cassette of claim 2.

5. The plant cell of claim 4, wherein said plant cell is from a monocot.

6. The plant cell of claim 5, wherein said monocot is maize.

7. The plant cell of claim 4, wherein said plant cell is from a dicot.

8. A plant having stably incorporated into its genome the expression cassette of claim 2.

9. The plant of claim 8, wherein said plant is a monocot.

10. The plant of claim 9, wherein said monocot is maize.

11. The plant of claim 8, wherein said plant is a dicot.

12. Transgenic seed of the plant of claim 8.

13. The plant of claim 8, wherein the heterologous nucleotide sequence of interest encodes a gene product that confers herbicide, salt, pathogen, or insect resistance.

14. A method for expressing a nucleotide sequence in a plant, said method comprising introducing into a plant cell an expression cassette comprising a promoter operably linked to a heterologous nucleotide sequence of interest, wherein said promoter comprises a nucleotide sequence having at least 99% sequence identity to the sequence set forth in SEQ ID NO:2, wherein said nucleotide sequence initiates transcription in a plant cell, wherein said initiation of transcription results in the expression of the heterologous nucleotide sequence of interest; and,
regenerating a transformed plant from said plant cell, wherein said plant has stably incorporated into its genome said expression cassette.

15. The method of claim 14, wherein said plant is a dicot.

16. The method of claim 14, wherein said plant is a monocot.

17. The method of claim 16, wherein said monocot is maize.

18. The method of claim 14, wherein said heterologous nucleotide sequence encodes a gene product that confers herbicide or pest resistance.

19. A method for expressing a nucleotide sequence in a plant cell, said method comprising introducing into a plant cell an expression cassette comprising a promoter operably linked to a heterologous nucleotide sequence of interest, wherein said promoter comprises a nucleotide sequence having at least 99% sequence identity to the sequence set forth in SEQ ID NO:2, wherein said nucleotide sequence initiates transcription in a plant cell, wherein said initiation of transcription results in the expression of the heterologous nucleotide sequence of interest.

20. The method of claim 19, wherein said plant cell is from a monocot.

21. The method of claim 20, wherein said monocot is maize.

22. The method of claim 19, wherein said plant cell is from a dicot.

23. The method of claim 19, wherein the heterologous nucleotide sequence encodes a gene product that confers herbicide or pest resistance.

24. The isolated nucleic acid molecule of claim 1, wherein said nucleotide sequence is selected from the group consisting of:
(a) the nucleotide sequence set forth in SEQ ID NO: 1, 2, 3, 5 or 6; and,
(b) the nucleotide sequence of the DNA insert of the plasmid deposited as Accession No. NRRL B-30819.

25. The method of claim 14, wherein said promoter comprises a nucleotide sequence selected from the group consisting of:
(a) the nucleotide sequence set forth in SEQ ID NO:1, 2, 3, 5 or 6; and,
(b) the nucleotide sequence of the DNA insert of the plasmid deposited as Accession No. NRRL B-30819.

26. The method of claim 19, wherein said promoter comprises a nucleotide sequence selected from the group consisting of:
(a) the nucleotide sequence set forth in SEQ ID NO:1, 2, 3, 5 or 6; and,
(b) the nucleotide sequence of the DNA insert of the plasmid deposited as Accession No. NRRL B-30819.

* * * * *

SEQUENCE LISTING

```
<160> NUMBER OF SEQ ID NOS: 6

<210> SEQ ID NO 1
<211> LENGTH: 2622
<212> TYPE: DNA
<213> ORGANISM: Tripsacum dactyloides

<400> SEQUENCE: 1
agccgccctc tttacgtttg gcacggttta tctgaatccg gcatggcaag ttagaccgca      60
gtgcagtgtg agccggccac cgcaagctag actgctgtgc tgtgccctc tctgaagagt      120 gaagactaaa ggccagccga tgagccgagc atggtgacag cagcatgacc ctatagtttt     180
tatctttctt agtgtgtgtg tgtgtgtgtg tgtgtgtgtg tgactatgtg agtaatgatt     240
ttagatctgt gagagggaca aaagaaataa tattgctaca tactttgaag gttgcggcat     300
ctttctccaa aatgttttgg tttgttgtct aaggactaag gcatttgaaa gtctaattgc     360
```

```
tcaagattcg acaattggga cgtcctaaag attagtaaat tctatagggt tgataacgtc    420
ttatttggct ggtccttttt tttttcatgt tccaactcta gttttttgga tgaaacttta    480
ccaaatacta acttaagaag taatttagga gagaagcttt aaagagtata atccattttt    540
atgctataag agtgaagtcg tcatcaatct agggtctgtt taggagagct tcacttcaag    600
aattttaggc tcgttccaac ttcttccatc taaacaggtc tagctccacg agctctaacc    660
ttgaaaaaaa aattgaaact agaagtcagc ttcatgaaat tcacgaagct ccccaagggg    720
tgcttcacaa acactaattt cataccttct catggagttg cacgagaact acccaccatg    780
tcaccgatta cacaacgtac cgcttcggct ctctcgtgac agctcactga tcatcaaggg    840
caatcaagga aactcacaaa atcaattttt attatagaag ctggagtccg cgcccaagcc    900
aaacactcct cgaactcacc ttaacaattt gttgaagcta ttttatgatg aaattggaaa    960
accgaagctg aaattttga agtaaaaccc tcacaaacag cctcgtagat cctgactgtt   1020 tttttttccca aaaagtttc acctatataa tactccatcc gccccaaaat atagttcttt   1080
ctagccctct tttttttcgt ccacatacaa atgaatgata ataaatctag acatacatat   1140
caaccacatt cttagattta ctaatgaatg tatgtttagt ctaaaaagaa tactattttg   1200
ggactgaggg agtaacaaat aaaaaaacta aagaaaccat gtacagtgag tggctttacc   1260
caattgccct cccctctaat cctttttttcc agtagataat gacaggcggg gctagttcaa   1320
cggcgtcgac gagtctaacg gaccacaacc agcgaaccac cagcgcgccg ggccaagcga   1380
agcagacggc acgggtatct ccgtcgctgc ctgtggaccc ctcccagag ttccgctcca   1440 ccggtggcgg tttccaagtc cattccgcat ttcgccgtc gcgttggact tgttccccgc   1500
tgtcggcatc cagaaattgc gtggcggagc ggcaggcggc aggcggcacg gcaggcggcc   1560
tcctcctcct tcgcagcacg gggggattcc tttcccaccg cccccttcgct ttcccttcct   1620 cgcccgccgt cataaataga caccccctcc tcagcctctt tccccaacct cagcttctct   1680
cgtgttgttc ggagcgcaca cacacacaac cagatctctt cccccaaatc tcctcgtcga   1740 tccccccccgc ttcaaggtac ggcgatcatc ctccctccct ctctctacct tctctagatc   1800
ggcgatccga tccatggtta gggcccggca attctgttcc tgtctgtgtt acatccgtgc   1860
tgctagtgtt cgtacatgga tgcgacctgt aaacggtaaa ccagacacgt tctggttgct   1920
aacttgtcag tactctttgg ggaatcctgg gatggctcta gccgttccgc agacgggata   1980
gatttcacga tttgcttttt ttttgttgtt gccgcctagg ttttgtttg cgttttttt   2040 ttattccgta tatgccgtgc tggtagatcg tgctacttac gttatgtgca cttgtttgtc   2100
gggtcatttt gtcatgtttt tttgttgttg tgatgatgtg gtctgattgg gctgtcgttc   2160
tagatcggag tagaataatg tgtcaaacta cctcgtagat ttttttaaaa aaaaattcgg   2220
atttgtatgt gtgtgtcata catcttcata gttaagaact taagatgatg gatgaaata   2280 tcgatcttta gataaggata ggtatacatg tcgatgtggg tttaactggt acctcggtag   2340
atgtattgct ctaacatgct ttagatgatg gcatatgcag catctgttca tatgctctaa   2400
catgctctaa ccttgagtac ctatctatca taataaacaa gtatgtttta taattatttg   2460
atcttgatac acttggatga tggtatatgc agcagctatg tcttgatttt tgccctgcct   2520
tcatgtgctg tttatttgct tgggactgtt cttttgttga tgctcaccct gtttggtgtt   2580
ccttctgcag atgcagatct tgtgaagac cctgactggc aa                       2622
```

<210> SEQ ID NO 2

<211> LENGTH: 2077
<212> TYPE: DNA
<213> ORGANISM: Tripsacum dactyloides

<400> SEQUENCE: 2

```
aagctttaaa gagtataatc cattttatg ctataagagt gaagtcgtca tcaatctagg      60
gtctgtttag gagagcttca cttcaagaat tttaggctcg ttccaacttc ttccatctaa    120
acaggtctag ctccacgagc tctaaccttg aaaaaaaaat tgaaactaga agtcagcttc    180
atgaaattca cgaagctccc caaggggtgc ttcacaaaca ctaatttcat accttctcat    240
ggagttgcac gagaactacc caccatgtca ccgattacaa acgtaccgc ttcggctctc    300
tcgtgacagc tcactgatca tcaagggcaa tcaaggaaac tcacaaaaat caattttatt    360
atagaagctg gagtccgcgc ccaagccaaa cactcctcga actcacctta acaatttgtt    420
gaagctattt tatgatgaaa ttggaaaacc gaagctgaaa tttttgaagt aaaaccctca    480
caaacagcct cgtagatcct gactgttttt tttcccaaaa aagtttcacc tatataatac    540
tccatccgcc ccaaaatata gttctttcta gccctctttt ttttcgtcca catacaaatg    600
aatgataata aatctagaca tacatatcaa ccacattctt agatttacta atgaatgtat    660
gtttagtcta aaaagaatac tattttggga ctgagggagt aacaaataaa aaaactaaag    720
aaaccatgta cagtgagtgg ctttacccaa ttgccctccc ctctaatcct ttttttccagt    780
agataatgac aggcggggct agttcaacgg cgtcgacgag tctaacggac cacaaccagc    840
gaaccaccag cgcgccgggc caagcgaagc agacggcacg ggtatctccg tcgctgcctg    900
tggacccctc cccagagttc cgctccaccg gtggcggttt ccaagtccat tccgcatttc    960
cgccgtcgcg ttggacttgt tccccgctgt cggcatccag aaattgcgtg gcggagcggc   1020
aggcggcagg cggcacggca ggcggcctcc tcctccttcg cagcacgggg ggattccttt   1080
cccaccgccc cttcgcttc ccttcctcgc ccgccgtcat aaatagacac cccctcctca   1140
gcctctttcc ccaacctcag cttctctcgt gttgttcgga gcgcacacac acacaaccag   1200
atctcttccc ccaaatctcc tcgtcgatcc ccccgcttc aaggtacggc gatcatcctc   1260
cctccctctc tctaccttct ctagatcggc gatccgatcc atggttaggg cccggcaatt   1320
ctgttcctgt ctgtgttaca tccgtgctgc tagtgttcgt acatggatgc gacctgtaaa   1380
cggtaaacca gacacgttct ggttgctaac ttgtcagtac tctttgggga atcctgggat   1440
ggctctagcc gttccgcaga cgggatagat ttcacgattt gcttttttt tgttgttgcc   1500
gcctaggttt ttgtttgcgt ttttttttta ttccgtatat gccgtgctgg tagatcgtgc   1560
tacttacgtt atgtgcactt gtttgtcggg tcattttgtc atgttttttt gttgttgtga   1620
tgatgtggtc tgattgggct gtcgttctag atcggagtag aataatgtgt caaactacct   1680
cgtagatttt tttaaaaaaa aattcggatt tgtatgtgtg tgtcatacat cttcatagtt   1740
aagaacttaa gatgatggat ggaaatatcg atctttagat aaggataggt atacatgtcg   1800
atgtgggttt aactggtacc tcggtagatg tattgctcta acatgcttta gatgatggca   1860
tatgcagcat ctgttcatat gctctaacat gctctaacct tgagtaccta tctatcataa   1920
taaacaagta tgttttataa ttatttgatc ttgatacact tggatgatgg tatatgcagc   1980
agctatgtct tgattttgc cctgccttca tgtgctgttt atttgcttgg gactgttctt   2040
ttgttgatgc tcaccctgtt tggtgttcct tctgcag                             2077
```

<210> SEQ ID NO 3
<211> LENGTH: 2077

<212> TYPE: DNA
<213> ORGANISM: Tripsacum dactyloides

<400> SEQUENCE: 3

| | | | | | |
|---|---|---|---|---|---|
| gcgctttaaa | gagtataatc | cattttatg | ctataagagt | gaagtcgtca | tcaatctagg | 60 |
| gtctgtttag | gagagcttca | cttcaagaat | tttaggctcg | ttccaacttc | ttccatctaa | 120 |
| acaggtctag | ctccacgagc | tctaaccttg | aaaaaaaaat | tgaaactaga | agtcagcttc | 180 |
| acgaaattca | cgaagctccc | caaggggtgc | tccacaaaca | ctaatttcat | accttctcat | 240 |
| ggagttgcac | gagaactacc | caccatgtca | ccgattacac | aacgtaccgc | ttcggctctc | 300 |
| tcgtgacagc | tcactgatca | tcgagggcaa | tcaaggaaac | tcacaaaaat | caattttatt | 360 |
| atagaagctg | gagtccgcgc | ccaagccaaa | cactcctcga | actcacctta | acaatttgtt | 420 |
| gaagctattt | tatgatgaaa | ttggaaaacc | gaagctgaaa | tttttgaagt | aaaaccctca | 480 |
| caaacagcct | cgtagatcct | gactgttttt | tttcccaaaa | aagtttcacc | tatataatac | 540 |
| tccatccgcc | ccaaaatata | gttctttcta | gccctctttt | ttttcgtcca | catacaaatg | 600 |
| aatgataata | atctagaca | tacatatcaa | ccacattctt | agatttacta | atgaatgtat | 660 |
| gtttagtcta | aaagaatac | tattttggga | ctgagggagt | aacaaataaa | aaaactaaag | 720 |
| aaaccatgta | cagtgagtgg | ctttacccaa | ttgccctccc | ctctaatcct | ttttccagt | 780 |
| agataatgac | aggcggggct | agttcaacgg | cgtcgacgag | tctaacggac | acaaccagc | 840 |
| gaaccaccag | cgcgccgggc | caagcgaagc | agacggcacg | ggtatctccg | tcgctgcctg | 900 |
| tggacccctc | cccagagttc | cgctccaccg | gtggcggttt | ccaagtccat | tccgcatttc | 960 |
| cgccgtcgcg | ttggacttgt | tccccgctgt | cggcatccag | aaattgcgtg | gcggagcggc | 1020 |
| aggcggcagg | cggcacggca | ggcggcctcc | tcctccttcg | cagcacgggg | ggattccttt | 1080 |
| cccaccgccc | cttcgctttc | ccttcctcgc | ccgccgtcat | aaatagacac | cccctcctca | 1140 |
| gcctcttttcc | ccaacctcag | cttctctcgt | gttgttcgga | gcgcacacac | acacaaccag | 1200 |
| atctcttccc | ccaaatctcc | tcgtcgatcc | ccccgcttc | aaggtacggc | gatcatcctc | 1260 |
| cctccctctc | tctaccttct | ctagatcggc | gatccgatcc | atggttaggg | cccggcaatt | 1320 |
| ctgttcctgt | ctgtgttaca | tccgtgctgc | tagtgttcgt | acatggatgc | gacctgtaaa | 1380 |
| cggtaaacca | gacacgttct | ggttgctaac | ttgtcagtac | tctttgggga | atcctgggat | 1440 |
| ggctctagcc | gttccgcaga | cgggatagat | ttcacgattt | gctttttttt | tgttgttgcc | 1500 |
| gcctaggttt | tgtttgcgt | tttttttta | ttccgtatat | gccgtgctgg | tagatcgtgc | 1560 |
| tacttacgtt | atgtgcactt | gtttgtcggg | tcattttgtc | atgttttttt | gttgttgtga | 1620 |
| tgatgtggtc | tgattgggct | gtcgttctag | atcggagtag | aataatgtgt | caaactacct | 1680 |
| cgtagatttt | tttaaaaaaa | aattcggatt | tgtatgtgtg | tgtcatacat | cttcatagtt | 1740 |
| aagaacttaa | gatgatggat | ggaaatatcg | atctttagat | aaggataggt | atacatgtcg | 1800 |
| atgtgggttt | aactggtacc | tcggtagatg | tattgctcta | acatgcttta | gatgatggca | 1860 |
| tatgcagcat | ctgttcatat | gctctaacat | gctctaacct | tgagtaccta | tctatcataa | 1920 |
| taaacaagta | tgttttataa | ttatttgatc | ttgatacact | tggatgatgg | tatatgcagc | 1980 |
| agctatgtct | tgattttttgc | cctgccttca | tgtgctgttt | atttgcttgg | gactgttctt | 2040 |
| ttgttgatgc | tcaccctgtt | tggtgttcct | tcgtcag | | | 2077 |

<210> SEQ ID NO 4
<211> LENGTH: 2077
<212> TYPE: DNA

<213> ORGANISM: Zea mays

<400> SEQUENCE: 4

```
ttatttattt agaaaaccag ctttgaccag ccgccctctt tacgtttggc acaatttagc     60
tgaatccggc ggcatggcaa ggtagactgc agtgcagcgt gacccggtcg tgcccctctc    120
tagagataat gagcattgca tgtctaagtt ataaaaaatt accacatatt ttttttgtca    180
cacttgtttg aagtgcagtt tatctatctt tatacatata tttaaacttt actctacgaa    240
taatataatc tatagtacta caataatatc agtgttttag agaatcatat aaatgaacag    300
ttagacatgg tctaaaggac aattgagtat tttgacaaca ggactctaca gttttatctt    360
tttagtgtgc atgtgttctc ctttttttttt ttgcaaatag cttcacctat ataatacttc    420
atccatttta ttagtacatc catttagggt ttagggttaa tggttttttat agactaattt    480
ttttagtaca tctatttttat tctattttag cctctaaatt aagaaaacta aaactctatt    540
ttagtttttt tatttaataa tttagatata aatagaata aataaagtg actaaaaatt    600
aaacaaatac cctttaagaa attaaaaaaa ctaaggaaac attttcttg tttcgagtag    660
ataatgccag cctgttaaac gccgtcgacg cagtctaacg acaccaacc agcgaaccag    720
cagcgtcgcg tcgggccaag cgaagcagac ggcacggcat ctctgtcgct gcctctggac    780
ccctctcgag agttccgctc caccgttgga cttcgtccgc tgtcggcatc cagaaattgc    840
gtggcggagc ggcagacgtg agccggcacg gcaggcggcc tcctcctcct ctcacggcac    900
cggcagctac gggggattcc tttcccaccg ctccttcgct ttcccttcct cgcccgccgt    960
aataaataga cacccctcc acaccctctt tccccaacct cgtgttgttc ggagcgcaca   1020
cacacacaac cagatctccc ccaaatccac ccgtcggcac ctccgcttca aggtacgccg   1080
ctcgtcctcc cccccctct ctaccttctc tagatcggcg ttccggtcca tggttagggc   1140
ccggtagttc tacttctgtt catgtttgtg ttagatccgt gtttgtgtta gatccgtgct   1200
gctagcgttc gtacacggat gcgacctgta cgtcagacac gttctgattg ctaacttgcc   1260
agtgtttctc tttggggaat cctgggatgg ctctagccgt tccgcagacg ggatcgattt   1320
catgattttt tttgtttcgt tgcatagggt ttggtttgcc cttttccttt atttcaatat   1380
atgccgtgca cttgtttgtc gggtcatctt ttcatgcttt tttttgtctt ggttgtgatg   1440
atgtggtctg gttgggcggt cgttctagat cggagtagaa ttctgtttca aactacctgg   1500
tggatttatt aattttggat ctgtatgtgt gtgccataca tattcatagt tacgaattga   1560
agatgatgga tggaaatatc gatctaggat aggtatacat gttgatgcgg ttttactga    1620
tgcatataca gagatgcttt tgttcgcttg gttgtgatga tgtggtgtgg ttgggcggtc   1680
gttcattcgt tctagatcgg agtagaatac tgtttcaaac tacctggtgt atttattaat   1740
tttggaactg tatgtgtgtg tcatacatct tcatagttac gagtttaaga tggatggaaa   1800
tatcgatcta ggataggtat acatgttgat gtgggtttta ctgatgcata tacatgatgg   1860
catatgcagc atctattcat atgctctaac cttgagtacc tatctattat aataaacaag   1920
tatgttttat aattattttg atcttgatat acttggatga tggcatatgc agcagctata   1980
tgtggatttt tttagccctg ccttcatacg ctatttattt gcttggtact gtttcttttg   2040
tcgatgctca ccctgttgtt tggtgttact tctgcag                           2077
```

<210> SEQ ID NO 5
<211> LENGTH: 2083
<212> TYPE: DNA
<213> ORGANISM: Tripsacum dactyloides

<400> SEQUENCE: 5

```
aagctttaaa gagtataatc catttttatg ctataagagt gaagtcgtca tcaatctagg    60
gtctgtttag gagagcttca cttcaagaat tttaggctcg ttccaacttc ttccatctaa   120
acaggtctag ctccacgagc tctaaccttg aaaaaaaaat tgaaactaga agtcagcttc   180
atgaaattca cgaagctccc caaggggtgc ttcacaaaca ctaatttcat accttctcat   240
ggagttgcac gagaactacc caccatgtca ccgattacac aacgtaccgc ttcggctctc   300
tcgtgacagc tcactgatca tcaagggcaa tcaaggaaac tcacaaaaat caattttatt   360
atagaagctg gagtccgcgc ccaagccaaa cactcctcga actcaccta acaatttgtt   420
gaagctattt tatgatgaaa ttggaaaacc gaagctgaaa tttttgaagt aaaaccctca   480
caaacagcct cgtagatcct gactgttttt ttccccaaaa aagtttcacc tatataatac   540
tccatccgcc ccaaaatata gttctttcta gccctctttt ttttcgtcca catacaaatg   600
aatgataata aatctagaca tacatatcaa ccacattctt agatttacta atgaatgtat   660
gtttagtcta aaagaatac tattttggga ctgagggagt aacaaataaa aaaactaaag   720
aaaccatgta cagtgagtgg ctttacccaa ttgccctccc ctctaatcct ttttttccagt   780
agataatgac aggcggggct agttcaacgg cgtcgacgag tctaacggac cacaaccagc   840
gaaccaccag cgcgccgggc caagcgaagc agacggcacg ggtatctccg tcgctgcctg   900
tggacccctc cccagagttc cgctccaccg gtggcggttt ccaagtccat tccgcatttc   960
cgccgtcgcg ttggacttgt tccccgctgt cggcatccag aaattgcgtg gcggagcggc  1020
aggcggcagg cggcacggca ggcggcctcc tcctccttcg cagcacgggg ggattccttt  1080
cccaccgccc cttcgctttc ccttcctcgc ccgccgtcat aaatagacac ccctcctca   1140
gcctctttcc ccaacctcag cttctctcgt gttgttcgga gcgcacacac acacaaccag  1200
atctcttccc ccaaatctcc tcgtcgatcc ccccgcttc aaggtacggc gatcatcctc  1260
cctccctctc tctaccttct ctagatcggc gatccgatcc atggttaggg cccggcaatt  1320
ctgttcctgt ctgtgttaca tccgtgctgc tagtgttcgt acatggatgc gacctgtgaa  1380
cggtaaacca gacacgttct ggttgctaac ttgtcagtac tctttgggga atcctgggat  1440
ggctctagcc gttccgcaga cgggatagat ttcacgattt gcttttttt tgttgttgcc   1500
gcctaggttt ttgtttgcgt tttttttta ttccgtatat gccgtgctgg tagatcgtgc   1560
tacttacgtt atgtgcactt gtttgtcggg tcattttgtc atgttttttt gttgttgtga  1620
tgatgtggtc tgattgggct gtcgttctag atcggagtag aataatgtgt caaactacct  1680
cgtagatttt tttaaaaaaa aattcggatt tgtatgtgtg tgtcatacat cttcatagtt  1740
aagaacttaa gatgatggat ggaaatatcg atctttagat aaggataggt atacatgtcg  1800
atgtgggttt aactggtacc tcggtagatg tattgctcta acatgcttta gatgatggca  1860
tatgcagcat ctgttcatat gctctaacat gctctaacct tgagtaccta tctatcataa  1920
taaacaagta tgttttataa ttacttgatc ttgatacact tggatgatgg tatatgcagc  1980
agctatgtct tgattttgc cctgccttca tgtgctgttt atttgcttgg gactgttctt  2040
ttgttgatgc tcaccctgtt tggtgttcct tttgcaggga tcc                    2083
```

<210> SEQ ID NO 6
<211> LENGTH: 2086
<212> TYPE: DNA
<213> ORGANISM: Tripsacum dactyloides

```
<400> SEQUENCE: 6
aagctttaaa gagtataatc cattttatg ctataagagt gaagtcgtca tcaatctagg       60
gtctgtttag gagagcttca cttcaagaat tttaggctcg ttccaacttc ttccatctaa      120
acaggtctag ctccacgagc tctaaccttg aaaaaaaaat tgaaactaga agtcagcttc      180
atgaaattca cgaagctccc caagggggtgc ttcacaaaca ctaatttcat accttctcat     240
ggagttgcac gagaactacc caccatgtca ccgattacac aacgtaccgc ttcggctctc      300
tcgtgacagc tcactgatca tcaagggcaa tcaggaaac tcacaaaaat caattttatt      360
atagaagctg gagtccgcgc ccaagccaaa cactcctcga actcacctta acaatttgtt      420
gaagctattt tatgatgaaa ttggaaaacc gaagctgaaa ttttttgaagt aaaaccctca     480
caaacagcct cgtagatcct gactgttttt tttcccaaaa aagtttcacc tatataatac     540
tccatccgcc ccaaaatata gttctttcta gccctctttt ttttcgtcca catacaaatg     600
aatgataata aatctagaca tacatatcaa ccacattctt agatttacta atgaatgtat     660
gtttagtcta aaagaatac tattttggga ctgagggagt aacaaataaa aaaactaaag      720
aaaccatgta cagtgagtgg ctttacccaa ttgccctccc ctctaatcct tttttccagt     780
agataatgac aggcggggct agttcaaggg cgtcgacgag tctaacggac acaaccagc      840
gaaccaccag cgcgccgggc caagcgaagc agacggcacg ggtatctccg tcgctgcctg     900
tggaccctc cccagagttc cgctccaccg gtggcggttt ccaagtccat tccgcatttc       960
cgccgtcgcg ttggacttgt tccccgctgt cggcatccag aaattgcgtg gcggagcggc    1020
aggcggcagg cggcacggca ggcggcctcc tcctccttcg cagcacgggg ggattccttt    1080
cccaccgccc cttcgctttc ccttcctcgc ccgccgtcat aaatagacac cccctcctca    1140
gcctctttcc ccaacctcag cttctctcgt gttgttcgga gcgcacacac acacaaccag    1200
atctcttccc ccaaatctcc tcgtcgatcc ccccgcttc aaggtacggc gatcatcctc     1260
cctccctctc tctaccttct ctagatcggg gatccgatcc atggttaggg cccggcaatt    1320
ctgttcctgt ctgtgttaca tccgtgctgc tagtgttcgt acatggatgc gacctgtaaa    1380
cggtaaacca gacacgttct ggttgctaac ttgtcagtac tctttgggga atcctgggat    1440
ggctctagcc gttccgcaga cgggatagat ttcacgattt gcttttttttt tgttgttgcc    1500
gcctaggttt ttgtttgcgt tttttttta ttccgtatat gccgtgctgg tagatcgtgc     1560
tacttacgtt atgtgcactt gtttgtcggg tcattttgtc atgttttttt gttgttgtga    1620
tgatgtggtc tgattgggct gtcgttctag atcggagtag aataatgtgt caaactacct    1680
cgtagatttt tttaaaaaaa aattcggatt tgtatgtgtg tgtcatacat cttcatagtt    1740
aagaacttaa gatgatggat ggaaatatcg atctttagat aaggataggt atacatgtcg    1800
atgtgggttt aactggtacc tcggtagatg tattgctcta acatgcttta gatgatggca    1860
tatgcagcat ctgttcatat gctctaacat gctctaacct tgagtaccta tctatcataa    1920
taaacaagta tgttttataa ttatttgatc ttgatacact tggatgatgg tatatgcagc    1980
agctatgtct tgattttgc cctgccttca tgtgctgttt atttgcttgg gactgttctt     2040
ttgttgatgc tcaccctgtt tggtgttcct tttgcaggac tagtcc                   2086
```